US010080782B2

(12) United States Patent
Abuchowski et al.

(10) Patent No.: US 10,080,782 B2
(45) Date of Patent: Sep. 25, 2018

(54) HEMOGLOBIN COMPOSITIONS

(75) Inventors: Abraham Abuchowski, Califon, NJ (US); Steven Sloshberg, Union, NJ (US); Keith O'Hare, East Windsor, NJ (US)

(73) Assignee: Prolong Pharmaceuticals, LLC, South Plainfield, NJ (US)

(*) Notice: Subject to any disclaimer, the term of this patent is extended or adjusted under 35 U.S.C. 154(b) by 278 days.

(21) Appl. No.: 12/797,582

(22) Filed: Jun. 9, 2010

(65) Prior Publication Data

US 2010/0311657 A1 Dec. 9, 2010

Related U.S. Application Data

(60) Provisional application No. 61/185,547, filed on Jun. 9, 2009.

(51) Int. Cl.
| | | |
|---|---|---|
| *A61K 38/42* | (2006.01) | |
| *A61K 47/60* | (2017.01) | |
| *A61K 47/02* | (2006.01) | |
| *A61K 9/00* | (2006.01) | |
| *A61K 9/08* | (2006.01) | |
| *A61K 41/00* | (2006.01) | |

(52) U.S. Cl.
CPC ............ *A61K 38/42* (2013.01); *A61K 9/0019* (2013.01); *A61K 9/08* (2013.01); *A61K 41/0009* (2013.01); *A61K 47/02* (2013.01); *A61K 47/60* (2017.08)

(58) Field of Classification Search
None
See application file for complete search history.

(56) References Cited

U.S. PATENT DOCUMENTS

| | | |
|---|---|---|
| 3,991,181 A | 11/1976 | Doczi |
| 4,401,652 A | 8/1983 | Simmonds et al. |
| 4,670,417 A * | 6/1987 | Iwasaki et al. ............... 514/13.5 |
| 4,831,012 A | 5/1989 | Estep |
| 4,857,636 A | 8/1989 | Hsia |
| 5,122,614 A | 6/1992 | Zaliipsky |
| 5,234,903 A | 8/1993 | Nho et al. |
| 5,264,555 A | 11/1993 | Shorr et al. |
| 5,281,579 A | 1/1994 | Estep |
| 5,281,698 A | 1/1994 | Nitecki |
| 5,386,014 A | 1/1995 | Nho et al. |
| 5,407,579 A | 4/1995 | Lee et al. |
| 5,478,806 A | 12/1995 | Nho |
| 5,558,985 A | 9/1996 | Chiang et al. |
| 5,565,427 A | 10/1996 | Fruedenberg |
| 5,585,484 A | 12/1996 | Acharya et al. |
| 5,605,884 A | 2/1997 | Lee et al. |
| 5,650,388 A | 7/1997 | Shorr et al. |
| 5,691,452 A | 11/1997 | Gawryl et al. |
| 5,763,401 A | 6/1998 | Nayar |
| 5,833,973 A | 11/1998 | Dobkowski et al. |
| 5,874,408 A | 2/1999 | Nayar |
| 5,962,650 A | 10/1999 | Österberg et al. |
| 5,972,885 A | 10/1999 | Spira et al. |
| 6,271,351 B1 | 8/2001 | Gawryl et al. |
| 6,329,176 B1 | 12/2001 | Wöldike et al. |
| 6,432,918 B1 | 8/2002 | Winslow |
| 6,437,102 B1 | 8/2002 | Lee et al. |
| 6,773,613 B1 | 8/2004 | Winslow et al. |
| 7,001,715 B2 | 2/2006 | Houtchens et al. |
| 7,601,201 B2 | 10/2009 | Fukutomi et al. |
| 7,759,306 B2 | 7/2010 | Simoni et al. |
| 7,932,356 B1 | 4/2011 | Wong et al. |
| 2004/0072729 A1* | 4/2004 | Kwang et al. .................... 514/6 |
| 2005/0026816 A1 | 2/2005 | Winslow et al. |
| 2005/0129747 A1 | 6/2005 | Barnikol et al. |
| 2005/0159339 A1 | 7/2005 | Acharya et al. |
| 2006/0135753 A1 | 6/2006 | Acharya et al. |
| 2006/0172924 A1 | 8/2006 | Winslow et al. |
| 2009/0298746 A1 | 12/2009 | Acharya et al. |
| 2010/0105606 A1 | 4/2010 | Winslow et al. |
| 2010/0311657 A1 | 12/2010 | Abushowski et al. |

FOREIGN PATENT DOCUMENTS

| | | |
|---|---|---|
| EP | 1 958 963 A1 | 8/2008 |
| JP | 62-089630 | 4/1987 |
| JP | 2-503676 A | 11/1990 |
| JP | 5-504133 A | 7/1993 |
| JP | 2007-269665 | 10/2007 |
| JP | 2008-511674 A | 4/2008 |
| WO | WO 1989/09784 | 10/1989 |
| WO | WO 1994/07510 | 4/1994 |
| WO | WO 1994/09027 | 4/1994 |
| WO | WO 1998/00441 | 1/1998 |
| WO | WO 1999/18979 | 4/1999 |
| WO | WO 2004/058291 | 7/2004 |
| WO | WO 2006/096774 A2 | 9/2006 |
| WO | WO 2010/144629 A1 | 12/2010 |

OTHER PUBLICATIONS

Conover, C.D., et al. 1999 Artif Cells Blood Substit Immobil Biotechnol 27(2): 93-107.*

(Continued)

*Primary Examiner* — Marsha M Tsay
(74) *Attorney, Agent, or Firm* — Crowell & Moring LLP

(57) ABSTRACT

The invention provides compositions containing hemoglobin, particularly PEGylated hemoglobin. The PEGylated hemoglobin molecule is capable of transferring oxygen or carbon monoxide bound thereto to a tissue with which it is in proximity. Exemplary PEGylated hemoglobin formulations of the invention are virally inactivated. Various compositions of the invention include deoxygenated hemoglobin, which may be conjugated with one or more water-soluble polymer. PEGylated hemoglobin includes those species in which the iron atom of the hemoglobin molecule is not bound to oxygen or any other species, and hemoglobin molecules in which a species other than oxygen, e.g., carbon monoxide, is bound to the iron atom. The compositions of the invention are formulated as hypo-, iso- or hypertonic solutions of the PEGylated hemoglobin. The compositions are of use to treat and/or ameliorate disease, injury and insult by providing for the oxygenation of tissues and/organs.

9 Claims, 7 Drawing Sheets

(56) References Cited

OTHER PUBLICATIONS

Brown, et al., "Water Systems for Pharmaceutical Facilities", *Pharmaceutical Engineering*, 11:15-23 (1991).
Cesar et al., "Plasma free fatty acid metabolism during storage of platelet concentrates for transfusion", *Transfusion*, 27(5): 434-437 (1987).
Kavida et al., "Theoretical analysis of effects of blood substitute affinity and cooperativity on organ oxygen transport", *J. Appl. Physiol.* 93:2122-2128 (2002).
Kilkson et al., "Platelet Metabolism During Storage of Platelet Concentrates at 22° C.", *Blood*, 64(2): 406-414 (1984).
Klaus et al., "Early Treatment of Transient Focal Cerebral Ischemia with Bovine PEGylated Carboxy Hemoglobin Transfusion", *Artificial Cells, Blood Substitutes, and Biotechnology*, Informa Healthcare (2010).
Koehler, R.C., "Experiments Performed on Cerebrovascular Effects of SANGUINATE™", *Department of Anesthesiology and Critical Care Medicine, John Hopkins University*, (Oct. 2010).
Leong et al., "Effects of a Combination Hemoglobin Based Oxygen Carrier-Hypertonic Saline Solution on Oxygen Transport in the Treatment of Traumatic Shock", *Resuscitation*, 82(7):937-43 (2011).
Murphy et al., "Improved Storage of Platelets for Transfusion in a New Container", *Blood*, 60(1): 194-200 (1982).
Murphy et al., "Platelet Storage at 22° C.: Role of Gas Transport Across Plastic Containers in Maintenance of Viability", *Blood*, 46(2): 209-218 (1975).
Murphy, S., "Platelet Storage for Transfusion", *Seminars in Hematology*, 22(3): 165-177 (1985).
Murphy, S., "The Preparation and Storage of Platelets for Transfusion", *Treatment of Bleeding Disorders With Blood Components, vol. I*, Mammon, Barnhart, Lusher, and Walsh, PJD Publications Ltd., Westbury, NY (Eds.) (1980).
Murphy, S., "Platelet Transfusion", *Progress in Hemostasis and Thrombosis, vol. 3*, T. Spacet, Gruton and Stratton, Inc. (Ed.) (1976).
Napolitano, L., "Hemoglobin-based Oxygen Carriers: First, Second or Third Generation? Human or Bovine? Where are we Now?"*Crit. Care Clin.*, 25: 279-301 (2009).
Natanson et al., "Cell-Free Hemoglobin-Based Blood Substitutes and Risk of Myocardial Infarction and Death—A Meta-analysis", JAMA, 299(19): 2304-2312 (2008).
Shen et al., "Improvements in Angiogenesis and Restoration of Blood Flow in Diabetic Mice by Sanguinate™", Poster presentation, Abstract (2011).
Silverman, T., "Guidance for Industry—Criteria for Safety and Efficacy Evaluation of Oxygen Therapeutics as Red Blood Cell Substitutes", *U.S. Department of Health and Human Services, Food and Drug Administration, Center for Biologics Evaluation and Research* (Oct. 2004).
Simon et al., "Extension of platelet concentrate storage", *Transfusion*, 23: 207-212 (1983).
Sims et al., "A Method for the Estimation of Polyethylene Glycol in Plasma Protein Fractions", *Anal. Biochem.*, 107: 60-63 (1980).
Stein, R., "FDA Faulted for Approving Studies of Artificial Blood Hemopure Made by Biopure", *Washington Post* (Apr. 29, 2008).
Villela et al., "Microcirculatory effects of red blood cells with different hemoglobin oxygen affinity in hemorrhagic shock", *The FASEB Journal*, Abstract 22:1227 (2008).
Brauer, P. et al., "Transcranial Doppler Sonography Mean Flow Velocity During Infusion of Ultrapurified Bovine Hemoglobin", *Journal of Neurosurgical Anesthesiology*, vol. 10, No. 3, pp. 146-152 (1998).
Han, J. et al., "Effect of Artificial Oxygen Carrier with Chemotherapy on Tumor Hypoxia and Neovasularization", *Artificial Cells, Blood Substitutes, and Biotechnology*, vol. 36, pp. 431-438 (2008).
Estep, T. N. et al., "Virus Inactivation in Hemoglobin Solutions by Heat", *Biomat. Art Cells, Art. Org.*, vol. 16, Nos. 1-3, pp. 129-134 (1988).
Fronticelli, et al., "Allosteric Modulation by Tertiary Structure in Mammalian Hemoglobins", The Journal of Biological Chemistry, 1995 vol. 270, No. 51, Dec. 22, pp. 30588-30592, American the American Society for Biochemistry and Molecular Biology, 1995. (Six (6) pages).
Natanson, et al., "Cell-Free Hemoglobin-Based Blood Substitutes and Risk of Myocardial Infarction and Death: A Meta-analysis", American Medical Association, JAMA, May 21, 2008, vol. 299, No. 19, pp. 2304-2312, with Cover page and Letters to the Editor section, retrieved from www.jama.com at Virginia Commonwealth University on Oct. 20, 2008, (Eleven (11) pages).
Vandegriff, et al., "CO-MP4, a polyethylene glycol-conjugated haemoglobin derivative and carbon monoxide carrier that reduces myocardial infarct size in rats", Pritish Journal of Pharmacology, 2008, vol. 154, pp. 1649-1661, Nature Publishing Group, 2008 (Thirteen (13) pages).
Ryter, et al., "Protective Functions of Heme Oxygenase-1 and Carbon Monoxide in the Respiratory System", Forum Review, Antioxidants and Redox Signaling, vol. 9, No. 12, 2007, pp. 2157-2173, Mary Ann Liebert, Inc., 2007 (Seventeen (17) pages).
English translation of Chinese Office Action issued in counterpart Chinese Application No. 201080025493.4 dated Jan. 13, 2016 (Four (4) pages).
European Office Action issued in European Application No. 10 727 289.0 dated Jul. 28, 2015 (five (5) pages).
Malaysian Office Action issued in counterpart Malaysian Application No. PI 2011005954 dated May 13, 2016 (Three (3) pages).
Canadian Office Action issued in counterpart Canadian Application No. 2,764,872 dated Feb. 10, 2016 (Five (5) pages).
Spanish-language Office Action issued in counterpart Mexican Application No. Mx/a/2011/013215 dated Mar. 29, 2016 (Two (2) pages).
Philippines Office Action issued in counterpart Philippines Application No. 1/2011/502565 dated Oct. 6, 2016 (Five (5) pages).
Taiwanese Office Action issued in counterpart Taiwanese Application No. 099118756 dated Jun. 7, 2016 with English translation (Ten (10) pages).
Korean-language Office Action issued in counterpart Korean Application No. 10 2012-7000555 dated Jul. 18, 2016 with English translation (Nineteen (19) pages).
Office Action issued in counterpart Australian Application No. 2015238812 dated Aug. 5, 2016 (Four (4) pages).
Japanese-language Office Action issued in counterpart Japanese Application No. 2015-232933 dated Aug. 10, 2016 with English translation (Seven (7) pages).
Canadian Office Action issued in counterpart Canadian Application No. 2,764,872 dated Mar. 22, 2017 (3 pages).
Japanese-language Office Action issued in counterpart Japanese Application No. 2012-515116 dated Jan. 31, 2017 with English translation (22 pages).
Fonticelli et al., "Design of Recombinant Hemoglobins for Use in Transfusion Fluids", Crit Care Clin vol. 25, 2009, pp. 357-371.
Japanese-language Office Action issued in counterpart Japanese Application No. 2015-232933 dated Apr. 4, 2017 with English translation (6 pages).
Robert M. Winslow, Vascular resistance and the efficacy of red cell substitutes in a rat hemorrhage model, J. Appl. Physiol. 85(3), 1998; pp. 993-1003.
Korean-language Office Action issued in counterpart Korean Application No. 10-2012-7000555 dated May 16, 2017 with English translation (5 pages).
Examination Report issued in counterpart Indian Application No. 4989/KOLNP/2011 dated Sep. 12, 2017 with English-language translation (5 pages).
Extended European Search Report issued in counterpart European Application No. 17188857.1 dated Nov. 17, 2017 (Nine (9) pages).
Philippine Office Action issued in counterpart Philippine Application No. 1/2011/502565 dated Nov. 16, 2017 (Three (3) pages).
Office Action issued in counterpart Taiwanese Application No. 099118756 dated Jun. 5, 2017 with English translation (Fifteen (15) pages).
Search Report issued in Taiwanese Application No. 099118756 dated Jun. 5, 2017 with English translation (2 pages).

(56) References Cited

OTHER PUBLICATIONS

Japanese-language Office Action issued in counterpart Japanese Application No. 2015-232933 dated Oct. 10, 2017 with English translation (Eleven (11) pages).
"Biomaterials, Artificial Cells, and Immobilization Biotechnology," 1992, vol. 20, Nos. 2-4, pp. 511-524 (Eighteen (18) pages).
Fox, Barbara F., "New Biotech Brings New Life to Old Drugs," PrincetonInfo, retrieved from URL: http://princetoninfo.com/index/php/component/us1more/?key=12-10-2008_BioTech, Dec. 10, 2008, issue of U.S. 1 Newspaper (Five (5) pages).
Kohler, Raymond C., "Experiments Performed on Cerebrovascular Effects of SANGUINATE," Johns Hopkins University, Oct. 22, 2010 (Seven (7) pages).
Korean-language Office Action issued in counterpart Korean Application No. 10-2017-7022846 dated Sep. 19, 2017 with English translation (Eight (8) pages).
Korean-language Office Action issued in counterpart Korean Application No. 10-2017-7000555 dated Sep. 19, 2017 with English translation (Thirteen (13) pages).
Japanese-language Office Action issued in counterpart Japanese Application No. 2015-232933 dated Jun. 15, 2018 (two (2) pages).
Japanese-language Office Action issued in counterpart Japanese Application No. 2017-145738 dated Apr. 18, 2018 with English translation (nine (9) pages).
Chile Office Action issued in Chile Patent Application No. 2011-003091 dated Jul. 23, 2018 (three pages).

\* cited by examiner

Stability of PEG-Hb at 37° C

HEMOGLOBIN COMPOSITIONS

CROSS-REFERENCE TO RELATED APPLICATIONS

This application claims priority to U.S. Provisional Patent Application Ser. No. 61/185,547, filed Jun. 9, 2010, which is incorporated herein by reference in its entirety for all purposes.

FIELD OF THE INVENTION

The present invention resides in the field of blood substitutes and resuscitation fluids, including polymer-modified protein, e.g., hemoglobin, formulations capable delivering oxygen or carbon monoxide to tissues.

BACKGROUND OF THE INVENTION

Trauma is one of the leading causes of death in the United States. The primary reason for the high mortality rate is the inability to maintain tissue oxygenation of the patient between the time of injury and time of surgery at a medical facility. The lack of oxygenation results in tissue damage, organ failure and death. Therefore, a major focus in treating traumatic shock is administering therapeutics providing as much oxygen as possible to internal tissues and organs of the patients.

An obvious approach to maintain oxygenation is blood transfusion. However, there are significant practical problems using blood in point of care treatment which make the routine use of stored human blood for use outside the medical facility impractical on a wide spread basis. Standard approaches to treat trauma primarily involve maintenance of intravascular circulating volume through administration of either isotonic, hypertonic, or hyperoncotic solutions. These treatments cannot uniformly increase oxygenation of internal tissues and organs enough to effectively prevent ischemia and organ failure.

As a consequence there is a major effort to develop hemoglobin based oxygen carriers (HBOCs) which are capable of restoring oxygen carrying capacity of trauma patients. HBOCs have a number of advantages over the use stored human blood, including a decreased chance of disease transmission, no immune reactivity, lack of a need for typing, and most importantly improved availability with decreased storage demands. A number of groups have developed HBOCs and several companies have conducted clinical trials to develop their hemoglobin based products as blood substitutes. Hemoglobin (HGB) isolated from human or animal blood, or a synthetically produced oxygen carrier, such as perfluorocarbon, are two types of blood substitutes that have been in clinical trials. Other red blood cell substitutes, have also been developed and characterized for use in patients. (See, for example, Red Blood Cell Substitutes, 1998, (Eds.) A. S. Rudolph, R. Rabinovici, and G. Z. Feuerstein, Dekker, New York, N.Y.). Such red blood cell substitutes may be used in conjunction with standard medical therapies, such as transfused blood or blood products. As a specific example, Enzon, Inc. (Piscataway, N.J.), has developed a polyethylene glycol (PEG)-modified bovine hemoglobin, abbreviated PEG-HGB. PEG-HGB is produced by a process in which strands of PEG are crosslinked to the surfaces of HGB molecules, for example, as disclosed in U.S. Pat. Nos. 5,386,014 and 5,234,903 to Nho et al.). Other specific examples include Hemopure™ and Oxyglobin (Biopure, Cambridge, Mass.). However none of these products have been established to produce significant increases in tissue oxygenation and none have received FDA approval, either because they are ineffective or produce significant toxicity.

Lack of suitable HBOCs has greatly hindered basic research into the physiology of tissue oxygenation and our understanding of the critical mechanisms involved in shock and its ensuing tissue damage. With regards to the HBOCs that have undergone clinical testing and produced significant toxicity, scarce information is available on the cause of these toxicities.

Thus, the methods for treating trauma induced hemorrhage are presently insufficient. While blood transfusion can restore oxygen to tissue and replenish lost circulating volume, use of blood as a means to treat hemorrhaging outside of medical facilities has significant practical problems. First of all there are generally limited quantities of blood available and for each person treated typing is necessary to prevent killing the patient through an immune reaction. However the most important problem in using blood to treat trauma patients outside of medical facilities is the storage and packaging constraints inherent in using this tissue. Thus, blood transfusions are not normally employed in point of care treatment of trauma patients.

In fact, the standard approaches to treat trauma primarily involve maintenance of intravascular circulating volume through administration of either isotonic, hypertonic, or hyperoncotic solutions. These approaches are intended to provide short term replenishment of circulatory volume and can also increase blood flow and hence oxygen delivery to tissues. However, when hemorrhage is severe, these treatments cannot uniformly increase oxygenation of internal tissues and organs enough to effectively prevent ischemia and organ failure. As a consequence, we have a high death rate from those individuals subject to severe trauma.

For years attempts have been made to develop hemoglobin based oxygen carriers (HBOCs) which are capable of providing oxygen to trauma patients. HBOCs have a number of advantages over the use stored human blood without many of the problems associated with using blood to treat trauma. These advantages include a decreased chance of disease transmission, no immune reactivity, lack of a need for typing, and most importantly improved availability with decreased storage demands. Ideally HBOCs should be able to bind oxygen and release it to needed tissues. It should be in a ready to use solution that is in a form that is stable for months under most environmental conditions especially those commonly encountered in point of care conditions in which trauma patients need treatment.

Over the years a number of attempts have been made to develop HBOCs as oxygen therapeutics using either native or recombinant human hemoglobin, modified forms of human hemoglobin or modified forms of hemoglobin from other species. Unmodified hemoglobin can be used as an oxygen therapeutic however it binds $NO_x$ and causes severe vasoconstriction and hypertension. As a consequence of its molecular weight, hemoglobin can cause significant toxicities, especially to the kidney where it clogs the glomerular apparatus. As a consequence, most hemoglobin's that have been tested in humans are modified to prolong their half life and reduce their toxicity.

It is an object of the invention to provide novel oxygen and carbon monoxide carrying and delivering molecules that can serve as blood substitutes and/or have therapeutic activity, and processes for the preparation of these molecules.

It is a further object of this invention to provide stabilized and virally inactivated hemoglobin and hemoglobin conjugates with water-soluble polymers useful as a therapeutic agents in transfusion medicine, the viral inactivation rendering the native hemoglobin and resulting hemoglobin formulations essentially free of transmissible infection agents. The conjugates are capable of delivering oxygen or carbon monoxide bound to the hemoglobin to tissues.

SUMMARY OF THE INVENTION

Amongst its many embodiments, the present invention provides a PEG-hemoglobin ("PEG-Hb") molecule, which can both carry and diffuse oxygen or carbon monoxide (CO) in the mammalian vasculature and into tissues in contact with the vasculature and/or in contact with the hemoglobin. The compositions of the invention include water-soluble, functional, deoxygenated, native hemoglobin. The composition includes a water-soluble hemoglobin fraction, which comprises a group of functional, native hemoglobin molecules. Each member of this group of hemoglobin molecules is in a deoxygenated state, is substantially free of chemical cross-linking agents and, in exemplary embodiments, has a $P_{50}$ of from about 22 mm Hg to about 26 mm Hg. The composition also includes a water-soluble stabilizer fraction. The stabilizer fraction aids in maintaining the group of hemoglobin molecules in a deoxygenated state. In various embodiments, the stabilizer fraction includes a stabilizing agent. Exemplary stabilizing agents have a structural element that is more reactive with oxygen (or reactive oxygen species (ROS)) than are the deoxygenated hemoglobin molecules. Optionally included in the composition is an aqueous diluent fraction. The diluent fraction includes a pharmaceutically acceptable diluent in which the hemoglobin fraction and the stabilizer fraction are soluble. In exemplary embodiments, the composition comprises less than 10% methemoglobin. In various embodiments, the compound is virally inactivated, rendering the composition essentially free of viral activity.

In exemplary embodiments, the invention provides a hemoglobin conjugate capable of transferring oxygen or carbon monoxide from the hemoglobin molecule to tissues in vivo (e.g., to tissues). The composition includes a covalent conjugate between a functional, deoxygenated, native hemoglobin molecule and at least one water-soluble polymer, e.g., poly(ethylene glycol), moiety. Hemoglobin is conjugated with a water-soluble polymer, e.g., PEGylated, because this modification prolongs the half-life of natural hemoglobin. This overcomes a major problem of short in vivo half-life of native hemoglobin itself, and of some of the previously developed HBOCs. Furthermore, by prolonging the half-life of hemoglobin, through the attachment of such polymers, the physical size of the molecule is increased. In exemplary embodiments, the conjugation leads to the formation of fewer breakdown products, reducing the chance of kidney toxicity found with native hemoglobin as well as with other, less stable HBOCs. PEGylation reduces immune recognition of hemoglobin. Thus, hemoglobin from non-human species can be utilized in the compositions and methods of the invention. In an exemplary embodiment, the hemoglobin is bovine hemoglobin. In exemplary embodiments, the composition is a virally inactivated hemoglobin conjugate composition.

In various embodiments, the composition includes a water-soluble hemoglobin fraction comprising a group of hemoglobin molecules. The group of hemoglobin molecules is deoxygenated and is covalently conjugated to at least one water-soluble polymer, e.g., poly(ethylene glycol), moiety. Exemplary water-soluble polymer conjugates are formed through covalently binding the water-soluble polymer to the polypeptide through an amine moiety of an amino acid residue, though it is within the scope of the present invention to form the conjugate through any hemoglobin amino acid residue. The hemoglobin conjugate in the hemoglobin fraction is substantially free of chemical cross-linking agents; and has a $P_{50}$ of from about 9 mm Hg to about 12 mm Hg. Exemplary compositions also include a water-soluble stabilizer fraction rendering the group of hemoglobin molecules oxidation resistant. The stabilizer fraction includes a stabilizing agent. Exemplary stabilizing agents include a structural element that prevents the reoxygenation of the deoxygenated hemoglobin. In various embodiments, the stabilizing agent is more reactive with oxygen than the members of the group of hemoglobin molecules. In various embodiments, that composition also includes a diluent fraction. Exemplary diluent fractions are pharmaceutically acceptable diluent in which the hemoglobin fraction is soluble. In an exemplary embodiment, the composition is essentially free of viral activity, and includes less than about 10% methemoglobin.

In various embodiments, the invention provides a virally inactivated hemoglobin composition comprising water-soluble, functional, deoxygenated, native hemoglobin. The composition is prepared by a method comprising, submitting a solution of deoxygenated hemoglobin and a stabilizing agent to a thermal viral inactivation process. The thermal viral inactivation process includes exposing the solution to a temperature elevated sufficiently to inactivate essentially all viral activity in the solution. The elevated temperature treatment is for a time sufficient to achieve the inactivation of essentially all viral activity in the solution. The stabilizing agent includes a structural element that prevents the reoxygenation of the deoxygenated hemoglobin. In an exemplary embodiment, this structural element is selected such that it is more reactive with oxygen or ROS than it is with the deoxygenated hemoglobin. The stabilizing agent serves the function of minimizing oxygen binding by the deoxygenated hemoglobin. In various embodiments, the solution includes an amount of the stabilizing agent sufficient to prevent formation of more than about 10% methemoglobin during the thermal viral deactivation process.

In exemplary embodiments, the invention provides a hemoglobin composition comprising water-soluble, functional, deoxygenated, native hemoglobin. This composition includes less than 10% methemoglobin. When the composition is virally inactivated, it is optionally prepared by a method comprising heating a precursor hemoglobin solution to about 60° C. for up to about 12 hours (e.g., from about 1 to about 4 hours). The precursor solution includes a stabilizing agent. The stabilizing agent includes a structural element that prevents the reoxygenation of the deoxygenated hemoglobin. In an exemplary embodiment, this structural element is selected such that it is more reactive with oxygen than it is with the deoxygenated hemoglobin. The stabilizing agent serves the function of minimizing oxygen binding by the deoxygenated hemoglobin.

In an exemplary embodiment, the invention provides a method of preparing hemoglobin composition of the invention. The composition includes water-soluble, functional, deoxygenated, native hemoglobin. In an exemplary embodiment, the composition includes a water-soluble hemoglobin fraction comprising a group of functional, native hemoglobin molecules wherein each member of the group of hemoglobin molecules is in a deoxygenated state; is substantially free of chemical cross-linking agents; and has a $P_{50}$ of from about 22 mm Hg to about 26 mm Hg. In various embodiments, the composition includes a water-soluble stabilizer fraction, which includes a stabilizing agent. The stabilizing agent includes a structural element that prevents the reoxygenation of the deoxygenated hemoglobin. In an exemplary embodiment, this structural element is selected such that it is more reactive with oxygen than it is with the deoxygenated hemoglobin. The stabilizing agent serves the function of minimizing oxygen binding by the deoxygenated hemoglobin, thereby maintaining the hemoglobin molecules in a deoxygenated state. In exemplary embodiment, the composition includes a diluent fraction. In various embodiments, the diluent fraction includes a pharmaceutically acceptable diluent in which the hemoglobin fraction is soluble. Various compositions are essentially free of viral activity, and comprise less than 10% methemoglobin. In an exemplary embodiment, the composition is virally inactivated. An exemplary method for preparing the virally inactivated composition includes submitting a mixture including the hemoglobin fraction and the stabilizer fraction to a thermal viral inactivation process. An exemplary thermal viral inactivation process includes exposing the mixture to a temperature elevated sufficiently to inactivate essentially all viral activity in the mixture. The period of time during which the mixture is at the elevated temperature is sufficient to achieve said inactivation of essentially all viral activity in said mixture.

In each of the compositions set forth above, the hemoglobin is optionally re-oxygenated. In one embodiment, the hemoglobin is reoxygenated following viral inactivation. Alternatively, the hemoglobin is bound to carbon monoxide. Binding to carbon monoxide can occur at essentially any point during preparation of the composition or after the composition is prepared. In an exemplary embodiment, in the deoxygenated composition, the Fe(II) of the hemoglobin is bound to carbon monoxide The present invention also provides methods of treating trauma, shock, ischemia and other illness that is amendable to amelioration by enhancing the oxygen or carbon monoxice content of tissues or organs. Compositions of the invention rapidly restore tissue oxygenation and fully repay oxygen debt in animal models of severe traumatic shock in which at least 50% of subjects normally die from hemorrhagic shock. Utilizing an exemplary formulation, a single unit of a composition of the invention repays the oxygen debt to all the major organs, opens the microvasculature and restores Mean Arterial Pressure. Various compositions of the invention are more effective and quicker in reversing oxygen debt than packed red blood cells. In an exemplary embodiment, a formulation of the invention repays at least 85%, at least 90%, at least 95% or at least 100% of oxygen debt in a subject in from about 60 minutes to about 160 minutes following administration of the formulation to the subject. Alternatively, the compositions of the invention increase the carbon monoxide concentration in a tissue. In an exemplary embodiment, the formulation paying back oxygen debt, or enhancing tissue carbon monoxide content, includes a PEGylated hemoglobin conjugate of the invention.

Thus, in an exemplary embodiment, the invention provides a method of delivering oxygen or carbon monoxide to a member selected from tissues and organs of a subject in need of such delivering. In an exemplary embodiment, the method includes administering to the subject an amount of a composition of any of the invention sufficient to accomplish the delivery of oxygen or carbon monoxide to one or more tissue and/or organ.

In various embodiments, the invention provides a method of reversing oxygen debt in a member selected from tissues and organs of a subject suffering from hemorrhagic shock. In an exemplary embodiment, the method includes administering to the subject an amount of a composition of any of the invention sufficient to reverse the oxygen debt. A similar method is provided for increasing the carbon monoxide content of a tissue, whether in response to a loss in carbon monoxide content due to disease, injury, etc., or as a means to gain therapeutic benefits from increasing carbon monoxide content in the tissue over the normal levels found in the tissue in a healthy or disease state.

In various embodiments, the invention provides a method of inducing angiogenesis in the tissues of a subject by administering to the subject an amount of a composition of the invention effective to induce angiogenesis. In exemplary embodiments, angiogenesis is induced in tissues suffering from oxygen deficiency. In further exemplary embodiments, the tissues or organs in which angiogenesis is induced are tissues or organs of a subject suffering from oxygen deficiency. In an exemplary embodiment, the method includes administering to the subject an amount of a composition of any of the invention sufficient to reverse the oxygen deficiency.

In various embodiments, the invention provides a method of increasing blood flow to tissues suffering from oxygen deficiency. The method consists of administering to the subject an amount of a composition of the invention effective to increase blood flow to the tissues suffering from oxygen deficiency. In an exemplary embodiment, the tissue or organ is a tissue or an organ of a subject suffering from poor blood flow. In an exemplary embodiment, the method includes administering to the subject an amount of a composition of any of the invention sufficient to reverse the poor blood flow.

In various embodiments, the invention provides a method of decreasing neurological damage and/or infarcted tissue in tissues suffering from oxygen deficiency. In an exemplary embodiment, the method includes administering to a subject and amount of a composition of the invention sufficient to decrease neurological damage and/or infract in the tissue suffering from oxygen deficiency. In an exemplary embodiment, the method includes administering to the subject an amount of a composition of any of the invention sufficient to reverse the amount of infracted and or neurologically damaged tissue.

In each of the embodiments set forth above, the hemoglobin in the formulation can be bound to oxygen, carbon monoxide or to neither. Moreover, the formulations in which the hemoglobin conjugate is incorporated can be hypotonic, isotonic or hypertonic relevant to the tonicity of the subjects blood.

Other embodiments, objects and advantages of the invention are apparent from the detailed description that follows.

DETAILED DESCRIPTION OF THE INVENTION

Introduction

Figure 1:
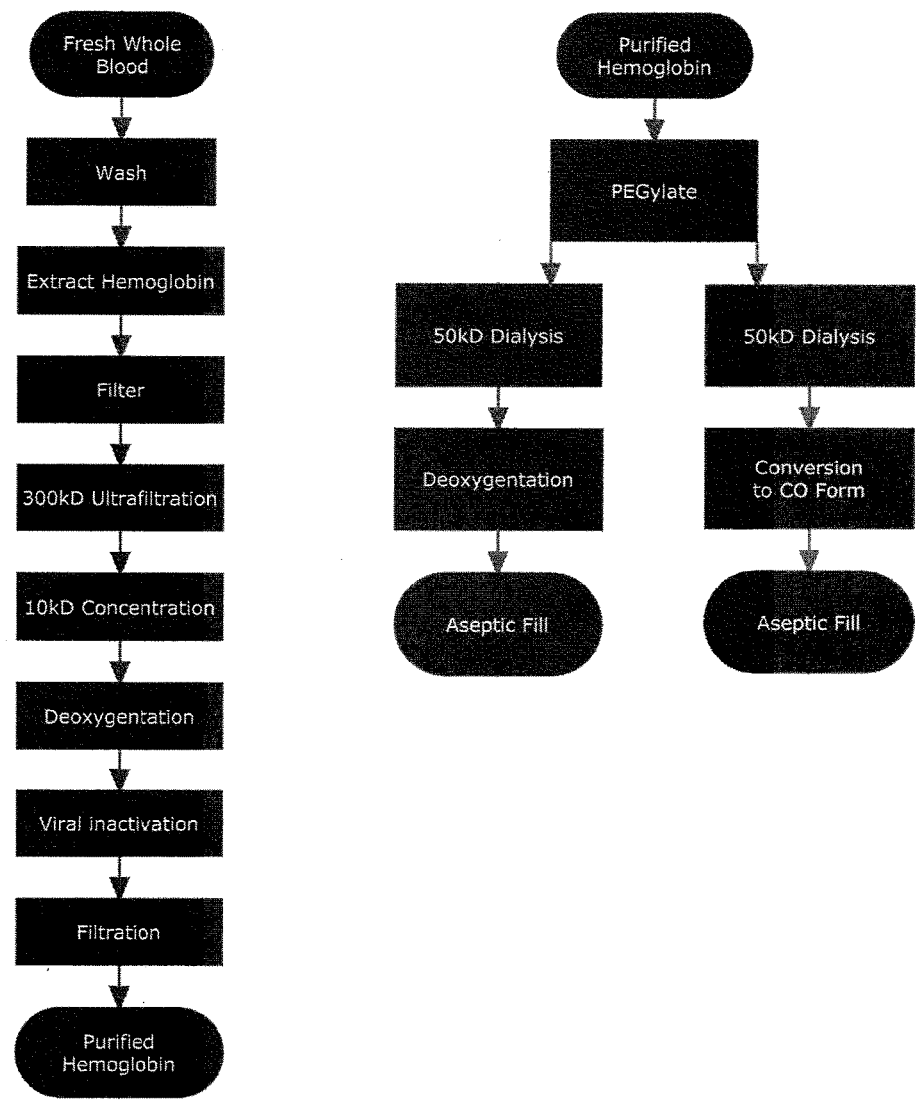
FIG. 1 is a flow chart of production of an exemplary PEG-Hb.
Figure 2:
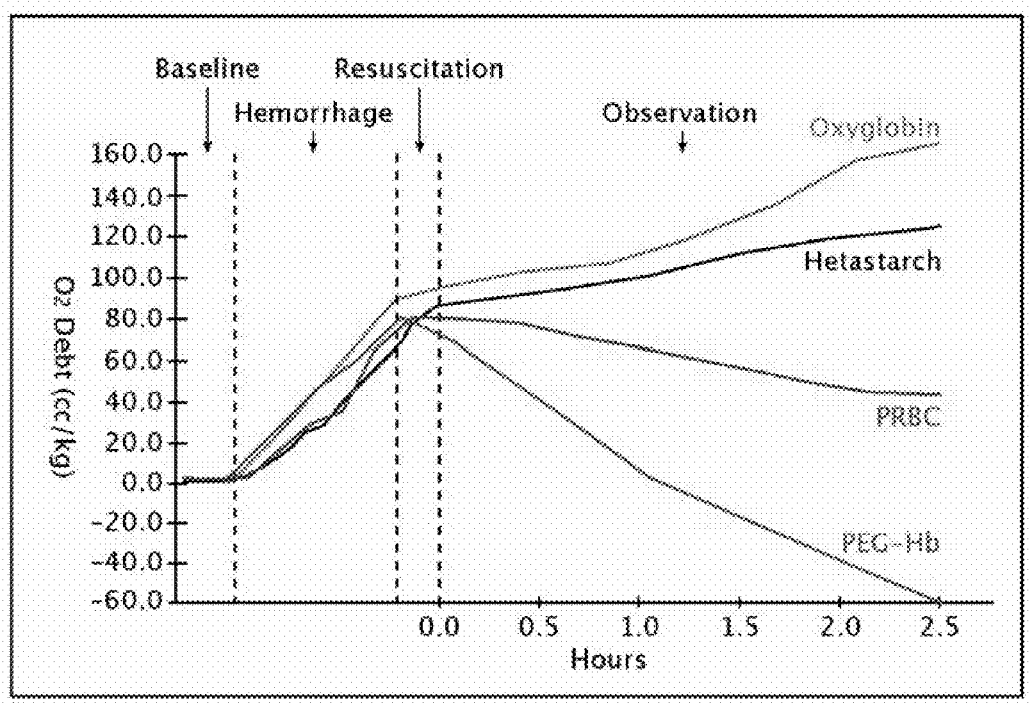
FIG. 2 is a graphic comparison of PEG-Hb/HS and other treatments to reverse oxygen debt in an animal model of traumatic shock.

There exists a need for an oxygen transfer agent to treat or prevent hypoxia resulting from disease, injury and insult, for example, blood loss (e.g, from acute hemorrhage or during surgical operations), resulting from anemia (e.g., pernicious anemia or sickle cell anemia), or resulting from shock (e.g, volume deficiency shock, anaphylactic shock, septic shock or allergic shock). The use of whole blood or blood fractions in these capacities is fraught with disadvantages. For example, the use of whole blood often is accompanied by the risk of transmission of any number of viruses, including hepatitis-producing viruses and AIDS-producing viruses, which can complicate patient recovery or result in patient fatalities. Additionally, the use of whole blood requires blood-typing and cross-matching to avoid immunohematological problems and inter donor incompatibility.

There also exists a need for therapeutic agents capable of delivering oxygen or carbon monoxide to tissues in a subject. The therapeutic agent is of use to treat, inter alia, conditions associated with blood loss, and ischemia.

The present invention meets both these needs by the provision of PEG-hemoglobin formulations in which the hemoglobin is bound to oxygen, bound to carbon monoxide or is bound to neither. The hemoglobin conjugate is formulated in a medium that is hypotonic, isotonic or hypertonic with respect to the tonicity of the blood of the subject to which the formulation is administered.

Human hemoglobin, as an oxygen delivery agent, a CO delivery agent and/or a blood-substitute, possesses osmotic activity and the ability to transport and transfer oxygen, but it has the disadvantage of rapid elimination from circulation by the renal route and through vascular walls, resulting in organ damage and a very short, and therefore, unsatisfactory half-life. Further, human hemoglobin is also frequently contaminated with toxic levels of endotoxins, bacteria and/or viruses.

Non-human hemoglobin suffers from the same deficiencies as human hemoglobin. In addition, hemoglobin from non-human sources has the potential to cause an immune system response in the recipient.

The present invention provides a hemoglobin formulation and methods of using this formulation to treat and ameliorate hypoxia due to disease, injury and insult, or to deliver CO to tissues in these states. Exemplary formulation are virally inactivated and in certain embodiments the hemoglobin is conjugated with a water-soluble polymer, e.g., PEGylated. Exemplary hemoglobin formulations of the invention include hemoglobin molecules with a $P_{50}$ that is different than that of naturally occurring human hemoglobin. The hemoglobin formulations of the invention reverse oxygen debt in trauma, as demonstrated in an animal model of severe trauma, indicating it has superior oxygen carrying capacity in vivo compared to other products. An exemplary formulation of the invention is able to rapidly restore tissue oxygenation and fully repay oxygen debt in trauma, as demonstrated in an animal model of severe traumatic shock in which at least 50% of subjects normally die from hemorrhagic shock. A single unit of an exemplary formulation of the invention repays the oxygen debt to all the major organs, opens the microvasculature and restores Mean Arterial Pressure. Exemplary formulations also provide superior stability and storage capacity over any other HBOC. An exemplary formulation is sufficiently stable to remain fully efficacious in an animal model after storage for at least 4 weeks at 45° C. (113° F.), an extreme environmental condition which validates that exemplary formulations of the invention are useful in point of care emergency situations.

Various formulations of the invention for clinical use include PEGylated hemoglobin, e.g., bovine hemoglobin, and isotonic or hypertonic saline (PEG-Hb/HS) and PEGylated hemoglobin in the CO form (PEG-Hb-CO) with or without high salt concentrations (i.e., isotonic or hypertonic). Exemplary formulations according to these embodiments increase the oxygen carrying capacity of blood via its hemoglobin content and enhance the delivery of oxygen to tissues by dilating the vasculature (through its hypertonic-oncotic actions or effect of CO) and by acting as an oxygen transfer agent between the red blood cell and the tissues. Exemplary formulations of the invention are also of use to treat sickle cell anemia, stroke or peripheral ischemia due to diabetes. An exemplary formulation includes PEG-Hb-CO, and is highly stable and has desirable pharmacological properties. In various embodiments, the PEG-Hb-CO has vasodilatory properties. In various embodiments, the PEG-Hb-CO has antioxidant properties. In various embodiments, the PEG-Hb formulations of the invention do not give rise to reactive oxygen species in a quantity sufficient to cause tissue damage. This formulation can be used to treat any of the diseases, insults or injuries discussed herein. In an exemplary embodiment, the formulation is used to treat ischemia. Exemplary types of ischemia treatable by this composition include cerebral ischemia and diabetic ischemia. Accordingly, the invention provides methods to treat, ameliorate and prevent the downstream damage from ischemic events. An exemplary type of ischemia treatable by compositions of the invention is peripheral ischemia, for example, peripheral diabetic ischemia.

Definitions

"CO" refers to carbon monoxide.

"HS" refers to high salt, a hypertonic formulation.

"Sanguinate™" as used herein refers to a PEG-HbCO composition of the invention.

The terms "blood substitute," "resuscitation fluid," "PEG-Hb," PEG-CO-Hb," "hemoglobin-based oxygen carrier" (HBOC) and "PEG-Hb/HS" refer to the PEGylated Hb compositions of the invention and formulations incorporating these compositions. The terms also carry with them the disclosure of an exemplary use of the composition and its formulation. For example, a "blood substitute" is of use to replace blood in the context of, e.g., trauma, stroke, ischemia/reperfusion injury, surgery, anemia or other injuries, insults and diseases in which a blood transfusion might be indicated. These terms, as used herein, also refer to Hb formulations capable of delivering oxygen or carbon monoxide to a tissue. These formulations are of use in injuries, insults and diseases characterized by the subject having adequate blood volume, yet the blood has inadequate ability to carry and/or deliver oxygen or carbon monoxide to tissues. The PEG-hemoglobin derivatives are formulated in hypotonic, isotonic or hypertonic salt solutions. Thus, exemplary deoxygenated PEG-Hb composition in which the Fe(II) is unbound or is bound to CO can be formulated in isotonic or hypertonic solution. Similarly, exemplary oxygenated PEG-Hb can be formulated in isotonic or hypertonic carriers.

The term "amino acid" refers to naturally occurring, e.g., cysteine, and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

"Peptide" and "polypeptide" refer to a polymer in which the monomers are amino acids and are joined together through amide bonds, alternatively referred to as a polypeptide. Additionally, unnatural amino acids, for example, β-alanine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer. The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983). An exemplary peptide is hemoglobin.

The term "peptide conjugate," and "hemoglobin conjugate" refer to species of the invention in which a hemoglobin polypeptide is conjugated with a water-soluble polymer, e.g., poly(ethylene glycol) (PEG), as set forth herein.

"Hemoglobin," as used herein refers to an oxygen-binding (or CO-binding), active polypeptide that is not chemically cross-linked through treatment with chemical cross-linking agents, e.g., dialdehydes, etc. An exemplary hemoglobin is the native protein with no modifications other than the conjugation of one or more PEG (e.g., m-PEG) moieties. As used herein, "substantially free of chemical cross-linking agents," refers to hemoglobin molecules that are not purposely cross-linked with chemical cross-linking agents. These hemoglobin preparations include less than 5%, less than 3% or less than 1% cross-linked hemoglobin.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed of a single amino acid, e.g., poly(lysine). An exemplary polysaccharide is poly(sialic acid). An exemplary poly(ether) is poly(ethylene glycol). Poly(ethylene imine) is an exemplary polyamine, and poly(acrylic) acid is a representative poly(carboxylic acid). The term "water soluble" as in a "water-soluble polymer" is a polymer that is soluble in water at room temperature. Typically, a solution of a water-soluble polymer will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

As used herein, the term "water-soluble polymer" includes those water-soluble polymers that are biocompatible and nonimmunogenic and specifically excludes any water-soluble polymer segments that are not biocompatible and nonimmunogenic. With respect to biocompatibility, a substance is considered biocompatible if the beneficial effects associated with use of the substance alone or with another substance (e.g., active agent) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble polymer segments described herein as well as conjugates are biocompatible and nonimmunogenic.

The polymer backbone of the water-soluble polymer can be poly(ethylene glycol) (i.e., PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a group of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly (ethylene glycol) can be represented in general form as $R(-PEG-OH)_m$ in which R represents the core moiety, such as glycerol or pentaerythritol, and m represents the number of arms. Multi-armed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as polypropylene glycol) ("PPG"), copolymers of ethylene glycol and propylene glycol and the like, poly(oxyethylated polyol), poly(olefinic alcohol), poly(vinylpyrrolidone), poly (hydroxypropylmethacrylamide), poly($\alpha$-hydroxy acid), poly(vinyl alcohol), polyphosphazene, polyoxazoline, poly (N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

Although the molecular weight of the water-soluble polymer (as well as the polymeric reagent utilized to form the conjugate) can vary, the molecular weight will satisfy one or more of the following values: greater than 100 Daltons; greater than 200 Daltons; greater than 400 Daltons; greater than 500 Daltons, greater than 750 Daltons; greater than 900 Daltons; greater than 1,000 Daltons, greater than 1,400 Daltons; greater than 1,500 Daltons, greater than 1,900 Daltons; greater than 2,000 Daltons; greater than 2,200 Daltons; greater than 2,500 Daltons; greater than 3,000 Daltons; greater than 4,000 Daltons; greater than 4,900 Daltons; greater than 5,000 Daltons; greater than 6,000 Daltons; greater than 7,000 Daltons; greater than 7,500 Daltons, greater than 9,000 Daltons; greater than 10,000 Daltons, greater than 11,000 Daltons; greater than 14,000 Daltons; greater than 15,000 Daltons; greater than 16,000 Daltons; greater than 19,000 Daltons; greater than 20,000 Daltons; greater than 21,000 Daltons; greater than 22,000 Daltons, greater than 25,000 Daltons; and greater than 30,000 Daltons. It is understood that the maximum limit of molecular weight for any given water-soluble polymer segment useful herein is about 300,000 Daltons.

The molecular weight of the water-soluble polymer (as well as the entire polymeric reagent used to form the conjugate) can also be expressed as being a value within a range of molecular weights. Exemplary ranges include: from about 100 Daltons to about 100,000 Daltons; from about 500 Daltons to about 80,000 Daltons; from about 1,000 Daltons to about 60,000 Daltons; from about 2,000 Daltons to about 50,000 Daltons; and from about 5,000 Daltons to about 40,000 Daltons.

Exemplary molecular weights for any given water-soluble polymer (as well as the entire polymeric reagent) within a polymeric reagent include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 40,000 Daltons, about 50,000 Daltons, about 60,000 Daltons, about 75,000 Daltons, and about 80,000 Daltons.

Those of ordinary skill in the art will recognize that the foregoing discussion concerning substantially water-soluble polymer is by no means exhaustive and is merely illustrative, and that all polymeric materials having the qualities described above are contemplated. As used herein, the term "polymeric reagent" generally refers to an entire molecule, which can comprise a water-soluble polymer and a functional group. The term "water-soluble polymer" is generally reserved for use in discussing one portion of a larger molecular structure such as a polymeric reagent, precursor molecule, conjugate, and so forth.

Each portion (e.g., functional group, active agent, water-soluble polymer, and so forth) of the polymeric reagent and other structures described herein can be directly attached to each other via a direct covalent bond. More typically, however, each portion is attached through a spacer moiety comprised of one or more atoms serving to tether each portion together into a unified whole.

Preferred spacer moieties through which the various portions of the polymeric reagents and other structures described herein include a chain of atoms made of carbon, nitrogen, oxygen, and/or sulfur atoms. Attached to this chain of atoms, can be one or more other atoms such as carbon, nitrogen, oxygen, sulfur, and hydrogen. The chain can be short and comprise as few as a chain of two to five atoms. Longer chains, for example, a chain of atoms of ten, fifteen, or more in length are also contemplated. In addition, the spacer moiety can comprise a ring of atoms that can be saturated, unsaturated, as well as being aromatic. When present, a spacer moiety preferably comprises a sequence of about 1-20 atoms excluding any branching atoms. Preferably, the atoms making up the spacer moiety (including any branching atoms) comprise some combination of oxygen, carbon, nitrogen, sulfur and hydrogen atoms. Spacer moieties can be of any useful format.

The term "half-life" or "t½", as used herein in the context of administering a drug to a patient, is defined as the time required for plasma concentration of a drug in a patient to be reduced by one half. Further explanation of "half-life" is found in Pharmaceutical Biotechnology (1997, D F A Crommelin and R D Sindelar, eds., Harwood Publishers, Amsterdam, pp 101-120). In an exemplary embodiment, the half-life of a PEG conjugate of the invention is between about 12 and about 22 hours, which is considerably longer than non-PEGylated hemoglobin.

As used herein, "pharmaceutically acceptable carrier" includes any material, which when combined with the conjugate retains the conjugate's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Exemplary carriers are hypertonic sodium chloride and isotonic sodium chloride (e.g., phosphate buffered saline). Hypertonic and isotonic carriers are of use in formulating deoxygenated PEGylated hemoglobin of the invention (e.g., carbon monoxide bound iron, and unbound iron) and PEGylated hemoglobin of the invention in which the iron atom is bound to oxygen.

As used herein, "administering," means intravenous, intraperitoneal, intramuscular, intralesional, or subcutaneous administration. Parenteral administration includes, e.g., intravenous, intramuscular, intra-arteriole, intradermal, subcutaneous, intraperitoneal, intraventricular, and intracranial.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters; including the results of a physical examination and/or a psychiatric evaluation.

The term "therapy" refers to "treating" or "treatment" of a disease or condition including providing relief from the symptoms or side-effects of the disease (including palliative treatment), and relieving the disease (causing regression of the disease). These terms also refer to the treatment of injury, including hemorrhagic shock, stroke, ischemia/reperfusion injury, trauma and the like. In various embodiments, these terms also refer to preventing the disease or condition from occurring in a subject that may be predisposed to the disease but does not yet experience or exhibit symptoms of the disease (prophylactic treatment), inhibiting the disease (slowing or arresting its development).

The term "effective amount" or "an amount effective to" or a "therapeutically effective amount" or any grammatically equivalent term means the amount that, when administered to a subject for treating a disease, condition or injury, is sufficient to effect treatment for that disease. In exemplary embodiments, this term refers to any amount of a conjugate of the invention (or a formulation including a conjugate of the invention) sufficient to repay at least 50%, at least 60%, at least 70%, at least 80%, at least 90% or up to about 100% of tissue or organ oxygen debt attributable to disease, insult or injury. When used in the context of delivery of CO to a tissue, this term refers to an amount administered sufficient to derive a detectable therapeutic effect from the delivery of CO to a tissue.

Exemplary hemoglobin composition of the invention are referred to as "capable of transferring a member selected from oxygen and carbon monoxide bound thereto to a tissue." This phrase refers to a hemoglobin composition having the capability to transfer oxygen or carbon monoxide bound to the iron atom of the hemoglobin to a tissue in. In exemplary compositions, the transfer is measureable by alteration in a tissue parameter (e.g., vasodilation, tissue oxygenation) or by a detectable alteration in a clinically relevant endpoint (e.g., termination of necrotic process, decreased ischemia/reperfusion injury). In an exemplary embodiment, the transfer of carbon monoxide or oxygen to a tissue is measured in terms of the amount of an oxygen debt "repaid" by administration of a selected volume of a composition of the invention to a subject (or tissue) with an oxygen debt. In another exemplary embodiment, the amount of oxygen or carbon monoxide delivered to a tissue is measured in terms of the mass of oxygen or CO transferred to a pre-selected mass of tissue (e.g., one gram) by administration of a pre-selected dosage of a composition of the invention. The ability to transfer oxygen or CO to a tissue can also be measured functionally in vivo, and by comparison with known hemoglobin-based blood substitutes. In an exemplary embodiment, the hemoglobin is in "contact" or "operative contact" with the tissue to which it is delivering oxygen or carbon monoxide. Bu operative contact is meant that the hemoglobin is sufficiently proximate to the tissue that the oxygen or carbon monoxide is transferred directly, through an intermediate carrier or through diffusion to the tissue.

As used herein, "native hemoglobin" refers to hemoglobin that is not intentionally chemically cross-linked or conjugated to another species. Native hemoglobin includes hemoglobin molecules in which the iron atom is unbound, is bound to oxygen or is bound to carbon monoxide. According to the present invention, native hemoglobin can form the hemoglobin core of the PEG-Hb conjugates of the invention.

"Deoxygenated" refers to hemoglobin in which the Fe(II) atom is bound to a species other than oxygen (e.g., carbon monoxide) or is not bound to oxygen or any other species.

The term "isolated" refers to a material that is substantially or essentially free from components, which naturally accompany the material, are used to produce the material or are side or degradation products from producing the material. For peptide conjugates of the invention, the term "isolated" refers to material that is substantially or essentially free from components which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%. The virally heat inactivated hemoglobin compositions of the invention are generally isolated prior to conjugation with a water-soluble polymer. In exemplary embodiments, the hemoglobin utilized to make the conjugate is isolated. In various embodiments, the hemoglobin PEG conjugate is isolated. In exemplary embodiments, the hemoglobin or PEG hemoglobin conjugate is isolated with the exception of the presence of a stabilizing agent or other excipients. In various embodiments, the hemoglobin or PEG hemoglobin conjugate is isolated from other proteins and particularly proteins selected from hemoglobin dimers or oligomers and other oxygen carrying proteins When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity. For the purposes of this invention a "pure" conjugate or solution of a pure conjugate can include a stabilizing agent.

Purity is determined by any art-recognized method of analysis (e.g., band intensity on a silver stained gel, polyacrylamide gel electrophoresis, HPLC, or a similar means).

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The expression, "each member of a group," is used to refer to the members of one subpopulation in a formulation of the invention having a particular characteristic. Thus, referring to each member of a group of hemoglobin molecules in a fraction of a formulation of the invention, does not necessarily imply that every hemoglobin molecule in the formulation has the recited characteristic, but refers to a group (subpopulation) of hemoglobin molecules in the formulation having the recited characteristic.

The term "stabilizing agent," refers to a species that prevents or retards the reoxygenation of deoxygenated hemoglobin. An exemplary stabilizing agent is an amine-containing compound, conveniently, though not exclusively, an amino acid. Any amine-containing compound can serve as a stabilizing agent in the formulations of the invention. An additional exemplary stabilizing agent has one or more structural elements that reacts with oxygen preferentially to the hemoglobin reacting with the oxygen. An exemplary structural element found on stabilizing agents of the invention is a thiol moiety. Exemplary sulfhydryl compounds of use as stabilizing agents include, but are not limited to, N-acetyl-L-cysteine (NAC) D,L-cysteine, γ-glutamyl-cysteine, glutathione, 2,3-dimercapto-1-propanol, 1,4-butanedithiol, and other biologically compatible sulfhydryl compounds. It is generally preferred that the stabilizing agent is bio-compatible and is non-toxic in the amounts in which it is included in the compositions and formulations of the invention. In an exemplary embodiment, the PEG is itself a stabilizing reagent. Thus, in various embodiments, the PEG conjugated to the Hb obviates the need for a separate stabilizing agent or a separate water-soluble stabilizing fraction. Accordingly, the invention provides formulations equivalent to those set forth herein including a water soluble stabilizing fraction, which, in fact, do not include this fraction.

As used herein, terms such as "subject," "patient," and "mammal" are used interchangeably, and are exemplified by a human.

As used herein a "nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo and/or are oxidized to produce nitric oxide and/or are substrates for nitric oxide synthase and/or cytochrome P450. "NO donor" also includes compounds that are precursors of L-arginine, inhibitors of the enzyme arginase and nitric oxide mediators.

The term "nitric oxide" encompasses uncharged nitric oxide (NO) and charged nitrogen monoxide species, preferably charged nitrogen monoxide species, such as nitrosonium ion ($NO^+$) and nitroxyl ion ($NO^-$). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose.

The terms "NO adducts, "NO precursor," and "NO-releasing agent" are used interchangeably.

In exemplary embodiments, the term "hypertonic" refers to a PEGylated Hb solution having from about 3% to about 7% salt.

The Embodiments

The discussion set forth below is germane to the embodiments set forth hereinbelow as well as those set forth above and in the attached claims. The elements of the embodiments are intended to be combined in any manner whatsoever, and the discussion presented herein is illustrative of exemplary combinations and is not limiting.

In an exemplary embodiment, the invention provides a composition comprising water-soluble, functional, deoxygenated, native hemoglobin. Exemplary compositions are virally inactivated. The composition includes a water-soluble hemoglobin fraction, which comprises a group of functional, native hemoglobin molecules. Each member of this group of hemoglobin molecules is in a deoxygenated state, is free of chemical cross-linking agents, and has a $P_{50}$ of from about 22 mm Hg to about 26 mm Hg. Alternatively, in various embodiments, the $P_{50}$ of the hemoglobin is from about 9 mm Hg to about 12 mm Hg). The composition also optionally includes a water-soluble stabilizer fraction. The stabilizer fraction aids in maintaining the group of hemoglobin molecules in a deoxygenated state. In various embodiments, the stabilizer fraction includes a stabilizing agent. Exemplary stabilizing agents have a structural element more reactive with oxygen than the deoxygenated hemoglobin molecules. Also included in the composition is an aqueous diluent fraction. The diluent fraction includes a pharmaceutically acceptable diluent in which the hemoglobin fraction and the stabilizer fraction are soluble. In various embodiments, the composition is essentially free of viral activity. In exemplary embodiments, the composition comprises less than 10% methemoglobin.

The Fe (II) of the deoxygenated hemoglobin of any of the species of the invention can be bound to CO or it can be essentially unbound to either oxygen or CO. In various embodiments, the Fe (II) of the deoxygenated hemoglobin molecules is bound to neither oxygen nor carbon monoxide. In various embodiments, the hemoglobin molecule is a member of a population of hemoglobin molecules. In this embodiment, an exemplary population of hemoglobin molecules includes less than 15%, 14%, 13%, 12%, 11%, 10%, 9%, 8%, 7%, 6%, 5%, 4%, 3%, 2% or less than 1% hemoglobin molecules in the oxygenated state.

The stabilizing fraction of the composition includes an agent that prevents or retards the oxidation of the deoxygenated hemoglobin. Any convenient and effective stabilizing agent can be used. In various embodiments, the stabilizing agent is one well-tolerated in biological systems and can be safely administered to mammals. An exemplary stabilizing agent in the stabilizing fraction is an amine, such as an amino acid, or a thiol compound. An exemplary stabilizing agent is a thiol-containing amino acid, amino acid analogue or amino acid mimetic. In various embodiments, the amino acid is selected from naturally occurring and non-naturally occurring amino acids, e.g., cysteine.

In various embodiments, the composition includes a pharmaceutically acceptable carrier, such as a diluent fraction comprising a salt. The salt can be selected from essentially any salt, though those salts presently preferred are salts that are pharmaceutically acceptable for delivery to mammal. In various embodiments, the composition includes sodium chloride. The compositions of the invention are isotonic, hypertonic or hypotonic. In various embodiments, the composition is hypertonic. In an exemplary embodiment, the composition included sufficient sodium chloride to render it hypertonic. In other embodiments, the diluent is tonic phosphate buffered saline.

In exemplary embodiments, the present invention provides hemoglobin fractions with essentially no synthetic cross-linking groups covalently joining two or more hemoglobin molecules. Though a small percentage of cross-links between hemoglobin molecules may be formed during production or storage of the compositions of the invention, these cross-linked species represent a small percentage of total hemoglobin and are not purposely prepared or selected for during purification. Accordingly, exemplary compositions of the invention typically include a population of hemoglobin molecules in which less than 10%, less than 5%, less than 4%, less than 3%, less than 2% or less than 1% of the total hemoglobin content is in the form of two or more hemoglobin molecules in a cross-linked state.

Hemoglobin of use in the present invention is derived from substantially any mammalian source. Exemplary sources of hemoglobin include common livestock animals, e.g., cows, pigs, sheep and the like. The invention is not limited by the source of the hemoglobin. In various embodiments, the hemoglobin is bovine hemoglobin.

The hemoglobin compositions of the invention include minimal amounts of methemoglobin. In various compositions, the amount of methemoglobin is less than 10%, less than 9%, less than 8%, less than 7%, less than 6%, less than 5%, less than 4%, less than 3%, less than 2% or less than 1%.

In an exemplary embodiment, the hemoglobin is isolated prior to being combined with the stabilizing fraction.

The invention provides covalent conjugates of hemoglobin with water-soluble polymers. Many water-soluble polymers are known to those of skill in the art and are useful in practicing the present invention. The term water-soluble polymer encompasses species such as saccharides (e.g., dextran, amylose, hyalouronic acid, poly(sialic acid), heparans, heparins, etc.); poly (amino acids), e.g., poly(aspartic acid) and poly(glutamic acid); nucleic acids; synthetic polymers (e.g., poly(acrylic acid), poly(ethers), e.g., poly(ethylene glycol)); peptides, proteins, and the like. The present invention may be practiced with any water-soluble polymer with the sole limitation that the polymer must include a point at which the remainder of the conjugate can be attached.

Thus in an exemplary embodiment, the invention virally inactivated hemoglobin composition, comprising a covalent conjugate between a functional, deoxygenated, native hemoglobin molecule and at least one water-soluble polymer moiety. The composition includes a water-soluble hemoglobin fraction including a group of hemoglobin molecules. Each member of the group of hemoglobin molecules is deoxygenated. In exemplary embodiments, the water-soluble polymer is covalently conjugated to the hemoglobin through an amine moiety of an amino acid residue. The hemoglobin is essentially free of introduced, chemical cross-linking agents. In various embodiments, the hemoglobin has a $P_{50}$ of from about 22 mm Hg to about 26 mm Hg. In various embodiments, the $P_{50}$ is from about 9 mm Hg to about 12 mm Hg. The composition also includes a water-soluble stabilizer fraction rendering the group of hemoglobin molecules oxidation resistant. The stabilizer fraction includes a stabilizing agent. Exemplary stabilizing agents include at least one structural element, which is more reactive with oxygen than the group of hemoglobin molecules. Various formulations also include a diluent fraction comprising a pharmaceutically acceptable diluent in which the hemoglobin fraction is soluble. Exemplary formulations are essentially free of viral activity, and comprise less than about 10% methemoglobin.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Molecular weight in the context of a water-soluble polymer of use in the compositions of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-pint depression, boiling-point elevation, or osmotic pressure) to determine number average molecular weight or the use of light scattering techniques, ultracentrifugation or viscometry to determine weight average molecular weight. The polymeric reagents of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03. Exemplary water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie*, 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly(ethylene glycols) are described in WO 96/21469, U.S. Pat. No. 5,932,462 describes a conjugate formed with a branched PEG molecule that includes a branched terminus that includes reactive functional groups.

The free reactive groups are available to react with a biologically active species, such as a protein or peptide, forming conjugates between the poly(ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

An exemplary water-soluble polymer is poly(ethylene glycol), e.g., methoxy-poly(ethylene glycol). The poly(ethylene glycol) used in the present invention is not restricted to any particular form or molecular weight range. For straight-chain poly(ethylene glycol) molecules the molecular weight is preferably between 500 and 100,000. A molecular weight of 2000-60,000 is preferably used and preferably of from about 5,000 to about 40,000. In an exemplary embodiment, the PEG used is a methoxy-PEG, with an average molecular weight of about 5,000.

In another embodiment the poly(ethylene glycol) is a branched PEG having more than one PEG moiety attached. Examples of branched PEGs are described in U.S. Pat. No. 5,932,462; U.S. Pat. No. 5,342,940; U.S. Pat. No. 5,643,575; U.S. Pat. No. 5,919,455; U.S. Pat. No. 6,113,906; U.S. Pat. No. 5,183,660; WO 02/09766; Kodera Y., *Bioconjugate Chemistry* 5: 283-288 (1994); and Yamasaki et al., *Agric. Biol. Chem.*, 52: 2125-2127, 1998. In a preferred embodiment the molecular weight of each poly(ethylene glycol) of the branched PEG is less than or equal to 40,000 daltons.

In various embodiments, the invention provides a hemoglobin conjugate having one or more PEG moieties bound thereto. The PEG-hemoglobin is in the CO form. In an exemplary embodiment, this conjugate is formulated in phosphate buffered saline.

In various embodiments, the invention provides a hemoglobin conjugate having one or more PEG moieties bound thereto. In various embodiments, the PEG-hemoglobin is deoxygenated and is not in the CO form. In other embodiments, the PEG-hemoglobin is in the CO form. In an exemplary embodiment, this conjugate, whether the PEG-Hb is in the oxygenated, CO or unbound form, is formulated in hypertonic saline (high salt). Exemplary salt (e.g., NaCl) concentrations of use in these hypertonic formulations are from about 4% to about 8%, from about 4.5% to about 7.5% or from about 5% to about 7%. Exemplary formulations include about 4%, about 5%, about 6%, about 7% or about 8% salt. In one formulation the salt concentration is 7.5%. In various embodiments, the salt is NaCl. In exemplary embodiments, the osmolality of the formulation is from about 300-400, or from about 325-375, or from about 340-360 mOsmol. In an exemplary embodiment the salt is NaCl.

In an exemplary embodiment, the invention provides a PEG-Hb-based resuscitation fluid having at least 75%, at least 80%, at least 85%, at least 90% at least 95% or about 100% of the efficacy equal to fresh frozen plasma in correcting coagulopathy. Exemplary formulations according to this embodiment further include coagulation factors, platelets or other substances known to aid in the mitigation of coagulopathy.

In various embodiments, the invention provides a PEG-Hb resuscitation fluid having a total fluid volume of about 450 mL, and which has an oxygen carrying and/or oxygen diffusion capacity equivalent to one unit of packed red blood cells, preferably human red blood cells.

In various embodiments, the invention provides a PEG-Hb formulation (e.g., a resuscitation fluid) capable of carrying CO and diffusing it into tissues. An exemplary formulation has a total fluid volume of about 450 mL, and which has a CO carrying and/or CO diffusion capacity sufficient to transfer a therapeutically relevant amount of CO to a tissue.

In an exemplary embodiment, the invention provides a PEG-Hb resuscitation fluid having coagulation factors present. In various embodiments, the coagulation factors are present in an amount not less than 60%, not less than 70%, not less than 80% or not less than 90% of fresh frozen plasma.

In an exemplary embodiment, the resuscitation fluid includes platelets. It is generally preferred that the resuscitation fluids of the invention including platelets have a cell count and activity that is not less than 60%, not less than 70%, not less than 80%, not less than 90% or is approximately equal to that of a single apheresis unit.

Stability to storage is an important object of the present invention. In various embodiments, the present invention provides a PEG-Hb resuscitation fluid that is stable at ambient temperature (~25° C.) for at least 4 months, at least six months, at least 9 months or at least 12 months.

The present invention also provides, in various embodiments, a PEG-Hb resuscitation fluid that is not more immunogenic than current banked blood products. Also provides is a PEG-Hb resuscitation fluid that is not more thrombogenic than current banked blood products.

Exemplary formulations according to the invention include one or more of these characteristics in any combination: about 4.0-4.6 wt % Hb, about 1.0-5.0 wt % Met, about 0.0-5.0% of $HbO_2$, about 95.0-100.0% of HbCO, a pH of about 8.10-8.20, osmolality of about 325-370 mOsmol, a P50 (mm Hg) of about 10.00-14.00, and an optical spectrum with major peaks at 538 nm and 568 nm with absorbance of about 1.4 and 1.9, respectively, a ratio of peaks at 568 nm/500 nm of 2.5-3.0. In other exemplary formulations, the formulation has an optical spectrum with major peaks at 541 and 576 nm.

Even more specifically, exemplary formulations of the invention include one or more of these characteristics in any combination: about 4.5 wt % Hb, about 1.1 wt % Met, about 1.2% $HbO_2$, about 99.4% HbCO, a pH of about 8.14, osmolality of about 356 mOsmol, a P50 (mm Hg) of about 12.2, and an optical spectrum with major peaks at 538 nm and 568 nm with absorbance of about 1,493 and about 1,465, respectively, and a ratio of peaks at 568 nm/500 nm of about 2.6.

Preparing the Conjugates
Preparation of Virally Deactivated Hemoglobin

Precursor hemoglobin of use in preparing the conjugates of the invention can be isolated from red blood cells (RBC). Suitable RBC sources include human blood, bovine blood, ovine blood, porcine blood, blood from other subjects and transgenically-produced hemoglobin, such as the transgenic Hb described in *BIO/TECHNOLOGY,* 12: 55-59 (1994).

The blood can be collected from live or freshly slaughtered donors. One method for collecting bovine whole blood is described in U.S. Pat. Nos. 5,084,558 and 5,296,465, issued to Rausch et al. It is preferred that the blood be collected in a sanitary manner.

Many methods are known in the art for the isolation and purification of hemoglobin; these methods are generally applicable to the compositions of the current invention. The discussion following herein is illustrative and not limiting.

In various embodiments, at or soon after collection, the blood is optionally mixed with at least one anticoagulant to prevent significant clotting of the blood. Suitable anticoagulants for blood are as classically known in the art and include, for example, sodium citrate, ethylenediaminetetraacetic acid and heparin. When mixed with blood, the anticoagulant may be in a solid form, such as a powder, or in an aqueous solution.

The blood solution can be strained prior to or during the anticoagulation step, for example by straining, to remove large aggregates and particles. A 600 mesh screen is an example of a suitable strainer.

The RBCs in the blood solution are then optionally washed by suitable means, such as by diafiltration or by a combination of discrete dilution and concentration steps with at least one solution, such as an isotonic solution, to separate RBCs from extracellular plasma proteins, such as serum albumins or antibodies (e.g., immunoglobulins (IgG)). It is understood that the RBCs can be washed in a batch or continuous feed mode.

Acceptable isotonic solutions are also known in the art and are of general utility in preparing the formulations of the invention. An exemplary isotonic solution has a neutral pH and an osmolarity between about 285-315 mOsm. Non-limiting examples of isotonic solution include solutions, such as a citrate/saline solution, having a pH and osmolarity which does not rupture the cell membranes of RBCs and which displaces the plasma portion of the whole blood. An exemplary the isotonic solution is composed of an aqueous solution of sodium citrate dihydrate (6.0 g/L) and of sodium chloride (8.0 g/L).

Water useful in the method of invention includes distilled water, deionized water, water-for-injection (WFI) and/or low pyrogen water (LPW). WFI, which is preferred, is deionized, distilled water that meets U.S. Pharmacological Specifications for water-for-injection. WFI is further described in Pharmaceutical Engineering, 11, 15-23 (1991). LPW, which is preferred, is deionized water containing less than 0.002 EU/ml.

RBCs in the blood solution can be washed by diafiltration. Suitable diafilters include microporous membranes with pore sizes which will separate RBCs from substantially smaller blood solution components, such as a 0.1 µm to 0.5 µm filter (e.g., a 0.2 µm filter). Concurrently, a filtered isotonic solution is added continuously (or in batches) as makeup at a rate equal to the rate (or volume) of filtrate lost across the diafilter. During RBC washing, components of the blood solution which are significantly smaller in diameter than RBCs, or are fluids such as plasma, pass through the walls of the diafilter in the filtrate. RBCs, platelets and larger bodies of the diluted blood solution, such as white blood cells, are retained and mixed with isotonic solution, which is added continuously or batchwise to form a dialyzed blood solution.

The RBCs can also be washed through a series of sequential (or reverse sequential) dilution and concentration steps, wherein the blood solution is diluted by adding at least one isotonic solution, and is concentrated by flowing across a filter, thereby forming a dialyzed blood solution.

RBC washing is complete when the level of plasma proteins contaminating the RBCs has been substantially reduced (typically at least about 90%). Additional RBC washing may further separate extracellular plasma proteins from the RBCs. For instance, diafiltration with 6 volumes of isotonic solution may remove at least about 99% of IgG from the blood solution.

The dialyzed blood solution is then optionally exposed to means for separating the RBCs in the dialyzed blood solution from the white blood cells and platelets, such as by centrifugation.

It is understood that other methods generally known in the art for separating RBCs from other blood components can be employed. For example, sedimentation, wherein the separation method does not rupture the cell membranes of a significant amount of the RBCs, such as less than about 30% of the RBCs, prior to RBC separation from the other blood components.

Following separation of the RBCs, the hemoglobin is extracted from the RBCs to form a hemoglobin-containing solution. Extraction can be performed by various methods including lysis and hypo-osmotic swelling of the RBCs. Lysis means one can use various lysis methods, such as mechanical lysis, chemical lysis, hypotonic lysis or other known lysis methods which release hemoglobin without significantly damaging the ability of the Hb to transport and release oxygen.

Alternatively, recombinantly produced hemoglobin, such as the recombinantly produced hemoglobin described in *Nature*, 356: 258-260 (1992), can be processed in the method of invention in place of RBCs. The bacteria cells containing the hemoglobin are washed and separated from contaminants as described above. These bacteria cells are then mechanically ruptured by means known in the art, such as a ball mill, to release hemoglobin from the cells and to form a lysed cell phase. This lysed cell phase is then processed as is the lysed RBC phase.

Following lysis, the lysed RBC phase is then optionally ultrafiltered to remove larger cell debris, such as proteins with a molecular weight above about 100,000 Daltons. Generally, cell debris includes all whole and fragmented cellular components with the exception of Hb, smaller cell proteins, electrolytes, coenzymes and organic metabolic intermediates. Acceptable ultrafilters include, for example, 100,000 Dalton filters.

Other methods for separating Hb from the lysed RBC phase can be employed, including sedimentation, centrifugation or microfiltration. The Hb filtrate can then be ultrafiltered to remove smaller cell debris, electrolytes, coenzymes, metabolic intermediates and proteins less than about 30,000 Daltons in molecular weight, and water from the Hb ultrafiltrate. Suitable ultrafilters include a 30,000 Dalton ultrafilter.

The concentrated Hb solution can then be directed into one or more parallel chromatographic columns to further separate the hemoglobin by high performance liquid chromatography from other contaminants such as antibodies, endotoxins, phospholipids and enzymes and viruses. Examples of suitable media include anion exchange media, cation exchange media, hydrophobic interaction media and affinity media. In one embodiment, chromatographic columns contain an anion exchange medium suitable to separate Hb from non-hemoglobin proteins. Suitable anion exchange mediums include, for example, silica, alumina, titania gel, cross-linked dextran, agarose or a derivatized moiety, such as a polyacrylamide, a polyhydroxyethylmethacrylate or a styrene divinylbenzene, that has been derivatized with a cationic chemical functionality, such as a diethylaminoethyl or quaternary aminoethyl group. A suitable anion exchange medium and corresponding eluants for the selective absorption and desorption of Hb as compared to other proteins and contaminants, which are likely to be in a lysed RBC phase, are readily determinable by one of reasonable skill in the art.

The Hb solution is optionally deoxygenated to form a deoxygenated Hb solution (hereinafter deoxy-Hb) by means that substantially deoxygenates the Hb without significantly reducing the ability of the Hb in the Hb eluate to transport and release oxygen, such as would occur from denaturation of formation of oxidized hemoglobin (metHb).

The Hb eluate can be deoxygenated by gas transfer of an inert gas across a phase membrane. Such inert gases include, for example, nitrogen, argon and helium. It is understood that other means for deoxygenating a solution of hemoglobin, which are known in the art, can be used to deoxygenate the Hb eluate. Such other means can include, for example, nitrogen sparging of the Hb eluate, chemical scavenging with reducing agents such as N-acetyl-L-cysteine (NAC), cysteine, sodium dithionite or ascorbate, or photolysis by light. The deoxygenated hemoglobin can be converted to the CO form.

Deoxygenation continues until the $pO_2$ of the Hb solution is reduced to a desired level, for example wherein the oxygenated Hb (oxyhemoglobin or $HbO_2$) content in the Hb solution is about 20% or less, 10% or less, 5% or less 3% or less or 1% or less.

During deoxygenation, the temperature of the Hb solution is typically maintained at a level that will balance the rate of deoxygenation against the rate of methemoglobin formation. Temperature is maintained to limit methemoglobin content to less than 20%. An optimum temperature will result in less than about 5% methemoglobin content, and preferably less than about 2.5% methemoglobin content, while still deoxygenating the Hb solution. Typically, during deoxygenation the temperature of the Hb solution is maintained between about 15° C. and about 35° C. During deoxygenation, and subsequently throughout the remaining steps of the method of invention, the Hb is maintained in a low oxygen environment to minimize oxygen absorption by the Hb The deoxygenated-Hb is optionally equilibrated with a low oxygen content storage buffer, containing a stabilizing agent, e.g., a sulfhydryl compound, to form an oxidation-stabilized deoxy-Hb. Suitable sulfhydryl compounds include non-toxic agents, such as N-acetyl-L-cysteine (NAC), D,L-cysteine, γ-glutamyl-cysteine, glutathione, 2,3-dimercapto-1-propanol, 1,4-butanedithiol, and other biologically compatible sulfhydryl compounds. An amount of sulfhydryl compound is added to establish a sulfhydryl concentration which will scavenge oxygen to maintain methemoglobin content less than about 15%, less than about 10%, or less than about 5% over the storage period. Typically, the amount of sulfhydryl compound added is an amount sufficient to establish a sulfhydryl concentration between about 0.05% and about 0.2% by weight.

The invention provides in various embodiments, a virally inactivated hemoglobin composition comprising water-soluble, functional, deoxygenated, native hemoglobin. The composition is prepared by a method comprising, submitting a solution of deoxygenated hemoglobin and a stabilizing agent to a thermal viral inactivation process. In an exemplary embodiment, the thermal viral inactivation process includes exposing the solution to a temperature elevated sufficiently to inactivate essentially all viral activity in said solution; the heat is elevated for a time sufficient to achieve the inactivation of essentially all viral activity in the solution. An exemplary stabilizing agent includes a structural element more reactive with oxygen than the deoxygenated hemoglobin in the solution, thereby minimizing oxygen binding by the deoxygenated hemoglobin. The solution includes an amount of the stabilizing agent sufficient to prevent formation of more than about 10%, 8%, 6%, 4% or 2% methemoglobin in the thermal viral deactivation process. In various embodiments, the stabilizing agent is selected to and is present in an amount sufficient to maintain methemoglobin concentration at about 5% or below.

In various embodiments, the composition includes a covalent conjugate between hemoglobin and at least at least 3, at least 4, at least 5, at least 6, at least 7, at least 8, at least 9, or at least about 10 water-soluble polymer moieties bound to the hemoglobin. The water-soluble polymers are bound to any appropriate residue on the hemoglobin. In an exemplary conjugate of the invention, one or more of the water-soluble polymer moieties is bound to an amino acid side chain, e.g., an ε-amine moiety of a lysine residue. In an exemplary embodiment, the invention provides a PEG-Hb conjugate as set forth above in which each Hb molecule is conjugated to 7, 8, 9 or 10 PEG moieties. In various embodiments, the invention provides a population of PEG-Hb conjugates in which the average number of PEG moieties per Hb molecule is from about 7 to about 10, or about 8 and about 9. In an exemplary embodiment, the PEG moiety is a PEG 5000 moiety.

Synthesis of the Conjugates

In various embodiments, the invention provides conjugates between one or more water-soluble polymer moiety and a hemoglobin polypeptide. In an exemplary embodiment, the precursor hemoglobin is a virally inactivated hemoglobin composition comprising water-soluble, functional, deoxygenated, native hemoglobin. The composition is prepared by a method comprising, submitting a solution of deoxygenated hemoglobin and a stabilizing agent to a thermal viral inactivation process. In an exemplary embodiment, the thermal viral inactivation process includes exposing the solution to a temperature elevated sufficiently to inactivate essentially all viral activity in said solution; the heat is elevated for a time sufficient to achieve the inactivation of essentially all viral activity in the solution. An exemplary stabilizing agent includes a structural element more reactive with oxygen than the deoxygenated hemoglobin in the solution, thereby minimizing oxygen binding by the deoxygenated hemoglobin. The solution includes an amount of the stabilizing agent sufficient to prevent formation of more than about 10%, 8%, 6%, 4% or 2% methemoglobin in the thermal viral deactivation process. In various embodiments, the stabilizing agent is selected to and is present in an amount sufficient to maintain methemoglobin concentration at about 5% or below.

In various embodiments, the precursor hemoglobin polypeptide is a virally inactivated hemoglobin composition comprising water-soluble, functional, deoxygenated, native hemoglobin. The composition comprises less than about 10% methemoglobin and is prepared by a method comprising heating a precursor hemoglobin solution to about 60° C. for up to about 12 hours, for example, from about 1 hour to about 4 hours. The precursor solution optionally includes a stabilizing agent. The stabilizing agent includes a structure that reacts more readily with oxygen or reactive oxygen species than do the hemoglobin molecules in the solution, thereby minimizing oxygen binding by the deoxygenated hemoglobin and, thereby forming said composition.

The conjugates between water-soluble polymers and the virally inactivated hemoglobin peptide can be formed by reaction of an activated derivative of the water-soluble polymer and the hemoglobin under suitable conditions. In various embodiments, the water-soluble polymer is conjugated to the hemoglobin through a side chain of an amino acid residue, for example, an ε-amine moiety of a lysine residue. Exemplary conjugates of the invention are include at least 3, at least 4, at least 5, at least 6, at least 7, at least 8, at least 9 or at least 10 water-soluble polymer moieties bound to the hemoglobin.

In an exemplary method of forming a conjugate of the invention, a precursor virally inactivated hemoglobin composition is oxygenated and the oxygenated hemoglobin is contacted with an activated water-soluble polymer molecule of reactivity complementary to an amino acid residue of the hemoglobin, thereby forming a covalent conjugate between the water-soluble polymer and oxygenated hemoglobin molecules in the oxygenated hemoglobin solution. In an exemplary embodiment, the hemoglobin of the covalent conjugate is deoxygenated or bound to CO. The deoxygenation can be mechanical or chemical, affording a hemoglobin molecule in which the iron is either unbound or is bound to CO.

In general, the water-soluble polymer (e.g., PEG) moiety and the polypeptide are linked together through the use of reactive groups, which are typically transformed by the linking process into a new organic functional group or species that is unreactive under physiologically relevant conditions. The reactive functional group(s) are located at any position on the peptide and water-soluble polymer. Reactive groups and classes of reactions useful in practicing the present invention are generally those that are well known in the art of bioconjugate chemistry. Currently favored classes of reactions available with reactive amino acid moieties are those, which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a hemoglobin polypeptide or water-soluble polymer include, but are not limited to:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides, or converted to thioethers, e.g., by reaction with maleimides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) maleimides, which can react with, for example, amines and sulfhydryls.

The reactive functional groups can be chosen such that they do not participate in, or interfere with, the reactions necessary to assemble the reactive polymeric modifying group (e.g., PEG). Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Suitable conjugation conditions are those conditions of time, temperature, pH, reagent concentration, reagent functional group(s), available functional groups on the active agent, solvent, and the like sufficient to effect conjugation between a polymeric reagent and an active agent. As is known in the art, the specific conditions depend upon, among other things, the active agent, the type of conjugation desired, the presence of other materials in the reaction mixture, and so forth. Sufficient conditions for effecting conjugation in any particular case can be determined by one of ordinary skill in the art upon a reading of the disclosure herein, reference to the relevant literature, and/or through routine experimentation.

For example, when the polymeric reagent contains an N-hydroxysuccinimide active ester (e.g., succinimidyl succinate, succinimidyl carbonate, succinimidyl propionate, and succinimidyl butanoate), and the active agent contains an amine group (e.g., a terminal amine group on a polypeptide and/or an epsilon amine of a lysine-containing polypeptide), conjugation can be effected at a pH of from about 7.5 to about 9.5 at room temperature. In addition, when the polymeric reagent contains a vinylsulfone reactive group or a maleimide group and the pharmacologically active agent contains a sulfhydryl group (e.g., a sulfhydryl group of a cysteine-containing or methionine-containing polypeptide), conjugation can be effected at a pH of from about 7 to about 8.5 at room temperature. Moreover, when the reactive group associated with the polymeric reagent is an aldehyde or ketone and the pharmacologically active agent contains a primary amine, conjugation can be effected by reductive amination wherein the primary amine of the pharmacologically active agent reacts with the aldehyde or ketone of the polymer. Taking place at pH's of from about 6 to about 9.5, reductive amination initially results in a conjugate wherein the pharmacologically active agent and polymer are linked via an imine bond. Subsequent treatment of the imine-containing conjugate with a suitable reducing agent such as NaCNBH$_3$ reduces the imine to a secondary amine.

Exemplary conjugation conditions include carrying out the conjugation reaction at a pH of from about 4 to about 10, and at, for example, a pH of about 4.0, 4.5, 5.0, 5.5, 6.0, 6.5, 7.0, 7.5, 8.0, 8.5, 9.0, 9.5, or 10.0. The reaction is allowed to proceed from about 5 minutes to about 72 hours, for example, from about 30 minutes to about 48 hours, for example, from about 4 hours to about 24 hours. The temperature under which conjugation can take place is typically, although not necessarily, in the range of from about 0° C. to about 40° C., and is often at room temperature or less. The conjugation reactions are often carried out using a phosphate buffer solution, sodium acetate, or a similar system.

With respect to reagent concentration, an excess of the polymeric reagent is typically combined with the hemoglobin. Exemplary ratios of polymeric reagent to hemoglobin include molar ratios of about 1:1 (polymeric reagent:hemoglobin), 5:1, 10:1, 15:1, 20:1, 25:1 or 30:1. in various embodiments, the conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymeric reagent remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess polymeric reagent, unconjugated reactants (e.g., active agent), and undesired multi-conjugated species. The resulting conjugates can then be further characterized using analytical methods such as MALDI, capillary electrophoresis, gel electrophoresis, and/or chromatography.

The polymer-hemoglobin conjugates can be purified to obtain/isolate different conjugated species. Alternatively, and more preferably for lower molecular weight (e.g., less than about 20,000 Dalton, more preferably less than about 10,000 Dalton) polymeric reagents used to form conjugates, the product mixture can be purified to obtain the distribution of water-soluble polymer segments per active agent. For example, the product mixture can be purified to obtain an average of a desired number of attachments of the polymeric reagent per Hb molecule, typically an average of about 7, 8, 9 or 10 attachments per Hb molecule. The strategy for purification of the final conjugate reaction mixture will depend upon a number of factors, including, for example, the molecular weight of the polymeric reagent employed, the particular Hb formulation, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymeric reagent-to-active agent ratios (e.g., 1-mer, 2-mer, 3-mer, and so forth, wherein "1-mer" indicates 1 polymeric reagent to active agent, "2-mer" indicates two polymeric reagents to active agent, and so on) on the basis of their differing molecular weights (where the difference corresponds essentially to the average molecular weight of the water-soluble polymer segments). For example, in an exemplary reaction where a 100,000 Dalton protein is randomly conjugated to a branched PEG having a total molecular weight of about 20,000 Daltons (wherein each polymer "arm" of the branched PEG has a molecular weight of about 10,000 Daltons), the resulting reaction mixture may contain unmodified protein (having a molecular weight of about 100,000 Daltons), monoPEGylated protein (having a molecular weight of about 120,000 Daltons), diPEGylated protein (having a molecular weight of about 140,000 Daltons), and so forth.

While this approach can be used to separate PEG and other polymer-active agent conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) Anal. Biochem, 107: 60-63), and (iv) sodium dodecyl sulfate polyacrylamide gel electrophoresis (SDS PAGE), followed by staining with barium iodide.

In various embodiments, the water-soluble polymer is PEG and it has a molecular weight of approximately 1 kD, 5 kD, 10 kD, 15 kD, 20 kD, 30 kD or 40 kD. The PEG moieties are linear or branched PEG species. The terminus of the PEG moiety, which is not attached to polypeptide (or to a linker attached to the polypeptide), can be either OH or another moiety, e.g., O—($C_1$-$C_4$) substituted or unsubstituted alkyl group. OMe (where Me is a methyl group) is presently preferred.

In an exemplary embodiment, the water-soluble polymer is a linear or branched PEG. In various embodiments, the conjugates include 1, 2, 3, 4, 5, 6, 7, 8, 9 or 10 PEG moieties per peptide. In an exemplary embodiment, the water-soluble polymer is a linear PEG and the conjugate includes approximately 6, 7, 8, 9 or 10 PEG moieties per peptide molecule. In another exemplary embodiment, the water-soluble polymer is a branched PEG and the conjugate includes approximately 1, 2, 3, 4 or 5 PEG moieties per peptide molecule.

In exemplary embodiments, in which the PEG is a linear species, the PEG moiety has a molecular weight which is from about 200 D to about 20 kD. In various embodiments, in which the PEG moiety is a linear PEG moiety, the molecular weight of the linear PEG is at least about 200 D, at least about 500 D, at least about 1 kD, at least about 2 kD, at least about 5 kD, at least about 10 kD, at least about 20 kD, at least about 30 kD or at least about 40 kD.

An exemplary PEG species of use in the invention is a branched PEG having two or more PEG arms. An exemplar of this embodiment is based on a side-chain amino acid, e.g., serine, cysteine or lysine and di-, tri- and tetra-peptides formed from these amino acids individually or in combination.

In other exemplary embodiments in which the PEG species is branched, the branched PEG includes from 2 to 6 linear PEG arms. Exemplary PEG arms have a molecular weight from about 200 D to about 30 kD. In various embodiments, each arm has an individually selected molecular weight that is at least about 2 kD, at least about 5 kD, at least about 10 kD, at least about 15 kD, at least about 20 kD, at least about 30 kD or at least about 40 kD.

In various embodiments, at least one poly(ethylene glycol) moiety is covalently conjugated through an amine moiety of an amino acid residue of the hemoglobin molecules. In an exemplary embodiment, the amino acid residue is a lysine residue and at least one poly(ethylene glycol) moiety is covalently conjugated to an ε-amine moiety of the lysine residue. Exemplary conjugation motifs are through a bond which is a member selected from an amide and a urethane.

Stability of the Conjugates

In various embodiments, the invention provides PEG-hemoglobin conjugates that are highly stable, as measured by their resistance to formation of methemoglobin. In one embodiment, the invention provides a conjugate that includes less than about 10%, 9%, 8%, 7%, 6%, 5%, 4% or 3% methemoglobin after storage at 45° C. for at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days.

In various embodiment, the invention provides PEG-hemoglobin conjugates that are highly stable, as measured by their resistance to formation of methemoglobin. In one embodiment, the invention provides a conjugate that includes less than about 10%, 9%, 8%, 7%, 6%, 5%, 4% or 3% methemoglobin after storage at 4° C. for at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, at least about 15 weeks, or at least about 16 weeks.

In various embodiments, the invention provides carbon monoxide (CO) form of the PEG-hemoglobin conjugate. This form appears to be particularly stable with regard to keeping % MET-Hb formation low as shown in Table 3. For example, the CO form showed only 4.0% % MET-Hb after storage at 37° C. for 16 weeks. This is more stable than the mechanically deoxygenated form.

An exemplary conjugate of the invention is fully efficacious in an animal model of hypovolemic shock after storage at 45° C. for at least about 3 weeks, at least about 4 weeks or at least about 5 weeks.

In an exemplary formulation according to each of the above descriptions, the hemoglobin of the conjugate is in the CO form. In various embodiments, the invention provides a PEG-Hb-CO conjugate that is stable at 4° C. for at least about 3 months, at least about 6 months, at least about 9 months or at least about 12 months.

Combination Formulations

In various exemplary embodiments, the invention provides combination formulations including one or more PEG-Hb conjugate or formulation of the invention in combination with another therapeutic agent or an agent that potentiates, complements or augments the activity of the PEG-Hb conjugate in the formulation. Exemplary agents include, but are not limited to, coagulants or precursors to coagulants, antioxidant enzymes, and agents that provide prophylaxis against or treat ischemia/reperfusion injury. Exemplary species according to these examples are set forth below.

In an exemplary embodiment, the invention provides a formulation including one or more PEG-Hb composition of the invention in combination with platelets.

Platelets are anucleate bone marrow-derived blood cells that protect injured mammals from blood loss by adhering to sites of vascular injury and by promoting the formation of plasma fibrin clots. Humans depleted of circulating platelets by bone marrow failure suffer from life threatening spontaneous bleeding, and less severe deficiencies of platelets contribute to bleeding complications following trauma or surgery.

A great deal is known about human platelet cells. General publications describing techniques, materials, and methods for the storage of platelets are described by Murphy et al., Blood 60(1):194-200 (1982); Murphy in "The Preparation and Storage of Platelets for Transfusion", Mammon, Barnhart, Lusher, and Walsh, PJD Publications, Ltd., Westbury, N.Y. (1980); Murphy in "Platelet Transfusion", Progress in Hemostasis and Thrombosis, Vol. III, Ed. by T. Spaet, Grune and Stratton, Inc. (1976); Murphy et al., Blood 46(2):209-218 (1975); Kilkson et al., Blood 64(2):406-414 (1984); Murphy in "Platelet Storage for Transfusion", Seminars in Hematology 22(3): 165-177 (1985); Simon et al., Transfusion 23:207-212 (1983); Cesar et al., Transfusion 27(5):434-437 (1987).

A reduction in the number of circulating platelets to below ~70,000 per μL reportedly results in a prolongation of a standardized cutaneous bleeding time test, and the bleeding interval prolongs, extrapolating to near infinity as the platelet count falls to zero. Patients with platelet counts of less than 20,000 per μL are thought to be highly susceptible to spontaneous hemorrhage from mucosal surfaces.

The platelet PEG-Hb formulations of the invention are of use to treat subjects suffering from bone marrow failure, e.g., aplastic anemia, acute and chronic leukemias, metastatic cancer but especially resulting from cancer treatment with ionizing radiation and chemotherapy. Moreover, the formulations are of use in the treatment and amelioration of thrombocytopenia associated with major surgery, injury (e.g., trauma) and sepsis.

The platelets and PEG-Hb formulation can be combined in any practical and efficacious manner. Thus, in an exemplary embodiment, the platelets and PEG-Hb are combined shortly before the resulting composition is administered to a subject. In other exemplary embodiments, the platelet-PEG-Hb formulation is prepared and stored for an appropriate time.

In various embodiments, the platelets, either alone or in combination with the PEG-Hb formulation are stabilized by a stabilizing agent. Exemplary stabilizing agents of use in the present invention are known in the art. See, for example, U.S. Pat. Nos. 7,241,282 and 5,466,573. The source of platelets is also optionally a blood composition enriched in platelets and fibrinogen such as that disclosed in U.S. Pat. No. 6,649,072.

In an exemplary embodiment, the invention provides a kit in which the two (or more) components are present and stored separately prior to their combination. For example, in various embodiments the invention provides a device for combining the platelets and PEG-Hb formulation. The device includes a first container for collecting or storing Factor(s); and at least one satellite container in fluid communication with the first container in which the PEG-Hb formulation is stored. In use, a break seal barrier is interposed between the first and satellite container such that upon rupture of the seal, the two components of the formulation can be mixed and subsequently administered to a subject in need thereof. As one of skill will appreciate, equivalents of the device described are available and fall within the spirit and scope of this disclosure. For example, a kit can include two or more ampoules, each containing an element of the combination formulation of the invention in liquid or dry form. The contents of the ampoules can be mixed at an appropriate time and in an appropriate manner prior to the administration of the combination formulation to a subject in need thereof.

In a further exemplary embodiment, the invention provides a formulation in which a PEG-Hb formulation of the invention is combined with one or more coagulation factor. Such formulations are of use in the treatment of certain coagulation disorders (e.g., a hereditary or acquired deficiency in blood coagulation), acute hemorrhage, and pre-surgery prophylaxis of bleeding amongst other uses.

In an exemplary embodiment, the invention provides a combination formulation including a PEG-Hb formulation of the invention and a coagulation factor which is a member selected from Factors II, V, VII, VIII, IX, X, XI, and XII and a combination thereof. In various exemplary embodiments, the Factor is selected from Factor VII, Factor VIII and Factor IX or a combination thereof.

Coagulation of blood is a complex process requiring the sequential interaction of a large number of components, nearly all of which are proteins. These components include fibrinogen and Factors II, V, VII, VIII, IX, X, XI, and XII. A lack of any of these components, or a nonfunctional component, can lead to an inability of the blood to clot when required, with resultant excessive and life-threatening blood loss to the patient.

The art is replete with established methods for preparation of coagulation factor concentrates various sorbents. For example, purification of the Factor VIII complex has resulted in Factor VIII preparations which have a purity level of about 90% or greater, and which are sufficiently stable for storage for long periods of time in a lyophilized form. See, for example, U.S. Pat. No. 4,650,858; and U.S. Pat. No. 5,399,670. Factor VIII formulations are also available. These include human factor VIII (like the active principles of Humate™, Monoclate™, Immunate™, and Hemofil™.), recombinant human factor VIII (like r-VIII SQ which is described in PCT patent application WO 91/09122 (the active principle of ReFacto™) or the active principles of Kogenate™ or Recombinate™), porcine factor VIII (which is the active principle of the product Hyate:C™) sold by Ipsen, Inc., USA) or recombinant porcine factor VIII (e.g. a modified B-domainless form of porcine factor VIII like the one disclosed in patent application WO 01/68109 and identified as "POL1212".

Additional Factor VIII formulations of use in the present invention include those disclosed in U.S. Pat. No. 5,565,427, U.S. Pat. No. 5,605,884, U.S. Pat. No. 5,763,401 U.S. Pat. No. 5,874,408, U.S. Pat. No. 5,962,650, U.S. Pat. No. 5,972,885, WO 89/09784, and WO 94/07510.

Other Factors are similarly available and of use in the present invention. In an exemplary embodiment, Factor VII is incorporated into a PEG-Hb formulation of the invention. Factor VII is a single chain glycoprotein (mol. wt. 50,000) of 406 amino acids that is secreted into the blood where it circulates in a zymogen form. In vitro, FVII can be proteolytically activated to activated Factor FVII, or FVIIa, by the action of activated coagulation factors Factor X (FXa), Factor IX (FIXa), Factor XII (FXIIa) or Factor II (FIIa). FVIIa does not promote coagulation by itself, but can complex with tissue factor (TF) exposed at the site of injury. The FVIIa/TF complex can convert FX to FXa, thereby inducing local hemostasis at the site of injury. Activation of FVII to FVIIa involves proteolytic cleavage at a single peptide bond between Arg-152 and Ile-153, resulting in a two-chain molecule consisting of a light chain of 152 amino acid residues and a heavy chain of 254 amino acid residues held together by a single disulfide bond.

Methods of producing and purifying Factor VII are known in the art. See, for example, U.S. Pat. No. 6,329,176. Some protein-engineered variants of FVII have been reported. See, e.g., Dickinson et al., *J. Bio. Chem.* 272: 19875-19879 (1997), Kemball-Cook et al., *J. Biol. Chem.* 273:8516-8521 (1998), Bharadwaj et al., *J. Biol. Chem.* 271:30685-30691 (1996), Ruf et al., Biochemistry, 38:1957-1966 (1999); WO 99/20767; WO 00/11416; WO 02/22776; WO 02/38162; WO 01/83725; WO 01/58935; and U.S. Pat. No. 5,580,560. FVII has been expressed in BHK and other mammalian cells (WO 92/15686, WO 91/11514 and WO 88/10295) and co-expression of FVII and kex2 endoprotease in eukaryotic cells (WO 00/28065). Commercial preparations of human recombinant FVIIa are sold as Novo-Seven™. NovoSeven™ is indicated for the treatment of bleeding episodes in hemophilia A or B patients.

Hemophilia B is caused by a deficiency of a blood plasma protein called Factor IX that affects the clotting property of blood. The disorder is caused by an inherited X-linked recessive trait, with the defective gene located on the X chromosome. Thus, the disorder occurs primarily in males. Human factor IX is a vitamin K-dependent zymogen which plays an important role in blood coagulation. Factor IX circulates as a 415-amino acid single chain zymogen with a molecular mass of 55,000 daltons and is present in normal plasma at approximately 5 µg/ml.

Several commercial forms of Factor IX concentrates are available to provide replacement therapy for patients suffering from hemophilia B. For example, blood-derived Factor IX complex products (containing other factors) are sold under the Bebulin VH™ (Baxter Healthcare, Vienna, Austria), konyne 80™ (Bayer Corporation, Elkhart Ind.), Profilnine SD™ (Alpha Therapeutic Corporation, Los Angeles Calif.), and Proplex™ (Baxter Healthcare, Glendale Calif.) brands. Somewhat more purified forms of Factor IX products are sold under the Alphanine SD™ (Alpha Therapeutic Corporation, Los Angeles Calif.) and Mononine™ (Aventis Behring, Kankakee Ill.) brands. With respect to recombinantly prepared Factor IX concentrates, one product, which is currently available is Benefix.™ (Wyeth/Genetics Institute, Cambridge Mass.).

Recombinant synthesis and purification of other coagulation factors and incorporation of these factors into a formulation of the invention is with the abilities of those of skill in the art.

The Factor(s) and PEG-Hb formulation can be combined in any practical and efficacious manner. Thus, in an exemplary embodiment, the Factor(s) and PEG-Hb are combined shortly before the resulting composition is administered to a subject. In other exemplary embodiments, the Factor(s)-PEG-Hb formulation is prepared and stored for an appropriate time.

In an exemplary embodiment, the invention provides a kit in which the two (or more) components are present and stored separately prior to their combination. For example, in various embodiments the invention provides a device for combining the Factor(s) and PEG-Hb formulation. The device includes a first container for collecting or storing Factor(s); and at least one satellite container in fluid communication with the first container in which the PEG-Hb formulation is stored. In use, a break seal barrier is interposed between the first and satellite container such that upon rupture of the seal, the two components of the formulation can be mixed and subsequently administered to a subject in need thereof. As one of skill will appreciate, equivalents of the device described are available and fall within the spirit and scope of this disclosure. For example, a kit can include two or more ampoules, each containing an element of the combination formulation of the invention in liquid or dry form. The contents of the ampoules can be mixed at an appropriate time and in an appropriate manner prior to the administration of the combination formulation to a subject in need thereof.

In another exemplary embodiment, the invention provides a combination formulation between a source of NO and a PEG-Hb formulation of the invention. This embodiment of the invention is illustrated by reference to various NO-donor molecules, however, one of skill will readily appreciate that the source of NO is not limited to these exemplary illustrations and other sources of NO can be incorporated into the combination formulation of the invention.

Nitric oxide (NO) is an important intracellular and intercellular messenger molecule that plays an important physiological role in anti-platelet aggregation and anti-platelet activation, vascular relaxation, neurotransmission, and immune response. NO (nitric oxide) is a biological "messenger molecule" which decreases blood pressure and inhibits platelet function, among other functions. NO freely diffuses from endothelium to vascular smooth muscle and platelet and across neuronal synapses to evoke biological responses.

Tissues deprived of blood and oxygen undergo ischemic necrosis or infarction with possible irreversible organ damage. Once the flow of blood and oxygen is restored to the organ or tissue (reperfusion), the organ does not immediately return to the normal pre-ischemic state. Post-ischemic dysfunction may be due to a variety of factors. Oxygen free radicals may play a role, as generation of free radicals in stunned myocardium has been demonstrated and free radical scavengers have been shown to attenuate contractile dysfunction. Impaired intracellular calcium handling and calcium overload during early reperfusion may contribute to post ischemic dysfunction.

It is well established that excessive oxidative stress due to free radicals may injure biological tissues. The natural defenses of cells and tissues revolve around antioxidant mechanisms that have evolved to protect the cells and tissues against high levels of oxidative stress. In our oxygen rich atmosphere the presence of oxygen at certain times of stress may be injurious; this has been termed the oxygen paradox and relates to the role of oxygen in generating and participating in free radical processes. In certain disease states associated with periods of restricted blood flow to tissues, such as heart attack, stroke and restricted flow to the extremities, intermittent episodes of no flow followed by re-flow of blood constitute ischemia/reperfusion (I/R) oxidative stress.

As used herein the term NO donor encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-allyl-2-((E)-hydroxyimino)-5-nitro-3-hexeneamines, N-((2Z, 3E)-4-ethyl-2-(hydroxyimino)-6-methyl-5-nitro-3-heptenyl)-3-pyridinecarbo-xamide (FR 146801), N-nitrosoamines, N-hydroxyl nitrosamines, nitrosimines, diazetine dioxides, oxatriazole 5-imines, oximes, hydroxylamines, N-hydroxyguanidines, hydroxyureas, benzofuroxanes, furoxans as well as substrates for the endogenous enzymes which synthesize nitric oxide.

Suitable NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-am-moniopropyl)-N-(n-propyl)amino)diazen-1-ium-1,2-diolate ("PAPA/NO"), (Z)-1-(N-(3-aminopropyl)-N-(4-(3-aminopropylammonio)butyl)-amino) diazen-1-ium-1,2-diolate (spermine NONOate or "SPER/NO") and sodium(Z)-1-(N, N-diethylamino)diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

Suitable furoxanes include, but are not limited to, CAS 1609, C93-4759, C92-4678, S35b, CHF 2206, CHF 2363, and the like.

Suitable sydnonimines include, but are not limited to, molsidomine (N-ethoxycarbonyl-3-morpholinosydnonimine), SIN-1 (3-morpholinosydnonimine) CAS 936 (3-(cis-2,6-dimethylpiperidino)-N-(4-methoxybenzoyl)-sydnonimine, pirsidomine), C87-3754 (3-(cis-2,6-dimethylpiperidino)sydnonimine, linsidomine, C4144 (3-(3, 3-dimethyl-1,4-thiazane-4-yl)sydnonimine hydrochloride), C89-4095 (3-(3,3-dimethyl-1,1-dioxo-1,4-thiazane-4-yl) sydnonimine hydrochloride, and the like.

Suitable oximes, include but are not limited to, NOR-1, NOR-3, NOR-4, and the like.

One group of NO adducts is the S-nitrosothiols, which are compounds that include at least one SNO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5-200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165-198 (1983), the disclosures of each of which are incorporated by reference herein in their entirety.

Another suitable NO donor class is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Another group of NO adducts for use in the invention, where the NO adduct is a compound that donates, transfers or releases nitric oxide, include compounds comprising at least one ONO or ONN group. The compounds that include at least one ONO— or ONN group are preferably ONO or ONN-polypeptides (the term "polypeptide" includes proteins and polyamino acids that do not possess an ascertained biological function, and derivatives thereof); ONO or ONN-amino acids (including natural and synthetic amino acids and their stereoisomers and racemic mixtures); ONO- or ONN-sugars; ONO or ONN modified or unmodified oligonucleotides (comprising at least 5 nucleotides, preferably 5-200 nucleotides); ONO or ON straight or branched, saturated or unsaturated, aliphatic or aromatic, substituted or unsubstituted hydrocarbons; and ONO, ONN or ONC-heterocyclic compounds. Preferred examples of compounds comprising at least one ON—O or ON—N group include butyl nitrite, isobutyl nitrite, tert-butyl nitrite, amyl nitrite, isoamyl nitrite, N-nitrosamines, N-nitrosamides, N-nitrosourea, N-nitrosoguanidines, N-nitrosocarbamates, N-acyl-N-nitroso compounds (such as, N-methyl-N-nitrosourea); N-hydroxy-N-nitrosamines, cupferron, alanosine, dopastin, 1,3-disubstitued nitrosiminobenzimidazoles, 1,3,4-thiadiazole-2-nitrosimines, benzothiazole-2(3H)-nitrosimines, thiazole-2-nitrosimines, oligonitroso sydnonimines, 3-alkyl-N-nitroso-sydnonimines, 2H-1,3,4-thiadiazine nitrosimines.

Another group of NO adducts for use in the invention include nitrates that donate, transfer or release nitric oxide, such as compounds comprising at least one $O_2NO$, $O_2NN$ or $O_2N$—S group. Preferred among these compounds are $O_2NO$, $O_2NN$— or $O_2NS$ polypeptides (the term "polypeptide" includes proteins and also polyamino acids that do not possess an ascertained biological function, and derivatives thereof); $O_2NO$, $O_2NN$ or $O_2NS$ amino acids (including natural and synthetic amino acids and their stereoisomers and racemic mixtures); ONO, $O_2NN$ or $O_2NS$ sugars; $O_2NO$—, $O_2NN$ or $O_2NS$ modified and unmodified oligonucleotides (comprising at least 5 nucleotides, preferably 5-200 nucleotides); $O_2NO$, $O_2NN$ or $O_2NS$ straight or branched, saturated or unsaturated, aliphatic or aromatic, substituted or unsubstituted hydrocarbons; and O—$_2NO$, $O_2NN$ or $O_2NS$ heterocyclic compounds. Preferred examples of compounds comprising at least one $O_2NO$, $O_2NN$ or $O_2NS$ group include isosorbide dinitrate, isosorbide mononitrate, clonitrate, erythrityl tetranitrate, mannitol hexanitrate, nitroglycerin, pentaerythrtoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883,122 and in WO 97/46521, WO 00/54756 and in WO 03/013432, the disclosures of each of which are incorporated by reference herein in their entirety.

Another group of NO adducts are N-oxo-N-nitrosoamines that donate, transfer or release nitric oxide and are represented by the formula: $R^{1"}R^{2"}NN(OM^+)NO$, where $R^{1"}$ and $R^{2"}$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M^+$ is an organic or inorganic cation, such, as for example, an alkyl substituted ammonium cation or a Group I metal cation.

In combination with the NO donor, the subject can be administered a therapeutically effective amount of a second compound that potentiates the therapeutic effect of NO. The second compound can be, for example, a phosphodiesterase inhibitor (e.g., 2-o-propoxyphenyl-8-azapurin-6-one [Zaprinast™], dipyridamole, theophylline, sildenafil [Viagra™], or 1,3-dimethyl-6-[2-propoxy-5-methanesulphonylamidophenyl]-pyrazolo[3,4-D]pyrimidin-4-[5H]-one) or superoxide dismutase. The second compound can alternatively be an antithrombotic agent such as ticlopidine, streptokinase, urokinase, t-PA or an analog thereof (e.g., met-t-PA, Retevase™, or FE1X), heparin, hirudin or an analog thereof (e.g., Hurulog.™), non-steroidal anti-inflammatory agent (e.g., indomethacin or aspirin), a glucocorticoid (e.g., prednisone), or a cytotoxic agent (e.g., methotrexate); or an anti-leukocyte agent such as an anti-leukocyte antibody.

Administration of nitric oxide has been used as a prophylaxis and treatment for ischemia/reperfusion injury. See, for example, U.S. Pat. No. 6,656,452 and references cited therein. Accordingly, it is a further object of this invention to provide formulations of hemoglobin based blood substitutes that include a source of NO for treatment of ischemia-reperfusion injury. In an exemplary embodiment, the blood substitute of the invention is combined with a NO-donor molecule. The combination can be at the time of manufacture of the blood substitute or at any point subsequent to the initial manufacture. For example the invention provides a two-compartment device or two separate containers. In one compartment or container the blood substitute is stored and in the second compartment or container an NO-donor molecule is supplied. Prior to administration to a subject in need thereof, the contents of the two compartments or containers are mixed and the resulting formulation is administered to the subject.

In various embodiments, the formulation of the invention further includes superoxide dismutase or catalase. These proteins are themselves optionally conjugated to a water-soluble polymer, e.g., PEG.

In an exemplary embodiment, the invention provides a formulation of use in treating, ameliorating, preventing or reducing ischemia/reperfusion injury and/or oxidative stress to one or more tissue of a subject to whom the formulation is administered.

In an exemplary embodiment, the invention provides a kit in which the two (or more) components are present and stored separately prior to their combination. For example, in various embodiments the invention provides a device for combining the NO donor and PEG-Hb formulation. The device includes a first container for collecting or storing the NO donor; and at least one satellite container in fluid communication with the first container in which the PEG-Hb formulation is stored. In use, a break seal barrier is interposed between the first and satellite container such that upon rupture of the seal, the two components of the formulation can be mixed and subsequently administered to a subject in need thereof. As one of skill will appreciate, equivalents of the device described are available and fall within the spirit and scope of this disclosure. For example, a kit can include two or more ampoules, each containing an element of the combination formulation of the invention in liquid or dry form. The contents of the ampoules can be mixed at an appropriate time and in an appropriate manner prior to the administration of the combination formulation to a subject in need thereof.

In each of the combination formulations set forth above, the PEG-Hb can be bound to oxygen, carbon monoxide or to neither. The PEG-Hb itself or the entire formulation can be formulated to be hypotonic, isotonic or hypertonic with respect to the tonicity of the subject's blood.

Methods of Use

There exists a need for a oxygen transfer agent to treat or prevent hypoxia resulting from blood loss (e.g, from acute hemorrhage or during surgical operations), resulting from anemia (e.g., pernicious anemia or sickle cell anemia), or resulting from shock (e.g, volume deficiency shock, anaphylactic shock, septic shock or allergic shock), myocardial infarct, stroke or traumatic brain injury. Additionally there is a need to hyper-oxygenate tumors to improve the therapeutic effect of radiation therapy or chemotherapy. The present invention provides compounds and methods, as exemplified hereinabove, useful for treating and preventing these and other conditions associated with blood loss, ischemia or hypoxia, for example.

Each of the formulations set forth herein is of use in a variety of methods for the treatment and prophylaxis of conditions associated with shock, hemorrhage, anemia or other dysfunctions of the oxygen carrying function of blood. The methods of the invention are of use to treat or prevent ischemia-reperfusion injury including those caused by surgery (e.g., transplantation surgery (especially kidney or heart transplantation surgery) or heart bypass surgery), thrombolysis, stroke, trauma-induced temporary hypotension, or a vascular interventional procedure such as atherectomy or angioplasty including the use of a laser, balloon, or stent. The methods can be used to treat or prevent ischemia-reperfusion injury after percutaneous transluminal coronary angioplasty. The injury treated or prevented can occur in any non-pulmonary tissue, including the kidney, heart, or brain Hypovolemic shock is a particular form of shock in which the heart is unable to supply enough blood to the body due to blood loss or inadequate blood volume. Loss of approximately one-fifth or more of the normal blood volume produces hypovolemic shock. The loss can be from any cause, including external bleeding (from cuts or injury), gastrointestinal tract bleeding, other internal bleeding, or from diminished blood volume resulting from excessive loss of other body fluids (such as can occur with diarrhea, vomiting, burns, and so on). In general, larger and more rapid blood volume losses result in more severe shock symptoms. In general, patients with milder degrees of shock tend to do better than those with more severe shock. However, in cases of severe hypovolemic shock, death is possible even with immediate medical attention. The elderly are at increased risk of having poor outcomes from shock.

In warfare, bullets and penetrating fragments from exploding munitions frequently cause life threatening hemorrhage. The Life Science Research Office estimates that exsanguinating hemorrhage was the mechanism of death for up to 50% of wounded soldiers who perished in past conflicts, and is considered to be the major cause of death in potentially salvageable battlefield casualties. Hemorrhage from wounded limbs alone has accounted for nearly one-tenth of all combat deaths, a portion of which were considered preventable had appropriate pre-hospital care been provided.

Anemia is the general term for any condition that develops when the blood is deficient in healthy red blood cells. Alternatively, there may be sufficient red blood cells but they are deficient in hemoglobin. Anemia is the most common blood condition in the U.S affecting about 3.5 million Americans. Women and people with chronic diseases are at increased risk of the condition. There are more than 400 types of anemia, which can be broadly classified into three categories: 1) anemia caused by blood loss, 2) anemia caused by decreased or faulty red blood cell production, or 3) anemia caused by destruction of red blood cells.

Regardless of the cause, there are a considerable number of individuals suffering from some form of clinical oxygen insufficiency that may be ameliorated by the use of a PEG-Hb formulation. The need for such a product and the commercial opportunities are almost endless. For example, Sickle cell anemia is the most common inherited blood disorder in the United States, affecting about 72,000 Americans. It is particularly painful and debilitating during crises. One can imagine treating these patients on a monthly basis with a single unit of PEG-Hb to prevent crisis and oxygenate tissues. This would require 864,000 units of PEG-Hb for this indication alone.

When capillaries or larger arteries become occluded, such as by vessel constriction or solid emboli that block or partially block the blood vessels, the oxygen supply becomes compromised for tissues that depend on those vessels for oxygen. Tissue hypoxia results from failure to transport sufficient oxygen, often due to inadequate blood flow i.e. ischemia. Hypoxia can result from internal hemorrhage (e.g., intracerebral hemorrhage producing cerebral hypoxia), anemia or trauma. Ischemia is a deficiency of oxygen supply to the tissue due to functional constriction or actual obstruction of a blood vessel. For example, myocardial ischemia is a deficiency of oxygen supply to heart muscle due to obstruction or constriction of the coronary arteries. If ischemia continues for more than a few seconds, tissue damage can result from a complex series of biochemical events associated with the ischemia-induced tissue hypoxia.

Hypoxic or ischemic conditions produced by emboli can result in tissue damage that is particularly debilitating if the damaged tissue is heart tissue or neural tissue of the central nervous system (CNS). The two most serious consequences of emboli are heart attack (acute myocardial infarct or AMI), resulting from cardiac muscle ischemia, and stroke, resulting from brain tissue ischemia. Ischemia which does not lead to AMI or stroke can, nonetheless, produce serious symptoms in the individual such as chest pains (angina pectoris), partial paralysis, confusion, disorientation and/or memory loss.

Individuals with vascular disease, particularly atherosclerosis, are particularly at risk for developing emboli that can result in AMI or stroke. Ischemic heart disease affects millions of people worldwide, often leading to sudden death by AMI. Ischemia can result when solid emboli produced from portions of plaque that dislodge and move through the circulatory system lodge in a capillary or attach to another plaque deposit in a blood vessel, thus fully or partially occluding the vessel or capillary. Atheromatous plaque particles can also be generated during vascular and cardiac surgery procedures (e.g. cannulation, clamping) that manipulate or disturb any atherosclerotic blood vessels (e.g., carotids, coronaries, aorta, femoral or popliteal vessels).

Accordingly, the present invention provides a method of delivering oxygen to a member selected from tissues and organs of a subject in need of such delivering. In an exemplary embodiment, the method includes administering to the subject an amount of a composition of any of the invention sufficient to accomplish the delivery of oxygen to one or more tissue and/or organ. In exemplary embodiments, the method is used to treat conditions such as hypoxia, ischemia, anemia and sickle cell anemia.

In various embodiments, the invention provides a method of reversing oxygen debt in a member selected from tissues and organs of a subject suffering from hemorrhagic shock. In an exemplary embodiment, the method includes administering to the subject an amount of a composition of any of the invention sufficient to reverse the oxygen debt.

In various embodiments, the invention provides a method of inducing angiogenesis in the tissues of a subject be administering to the subject an amount of a composition of the invention effective to induce angiogenesis. In exemplary embodiments, angiogenesis is induced in tissues suffering from oxygen deficiency. In further exemplary embodiments, the tissues or organs in which angiogenesis is induced are tissues or organs of a subject suffering from oxygen deficiency. In an exemplary embodiment, the method includes administering to the subject an amount of a composition of any of the invention sufficient to reverse the oxygen deficiency In various embodiments, the invention provides a method of increasing blood flow to tissues suffering from oxygen deficiency. The method consists of administering to the subject an amount of a composition of the invention effective to increase blood flow to the tissues suffering from oxygen deficiency. In an exemplary embodiment, the tissue or organ is a tissue or an organ of a subject suffering from poor blood flow. In an exemplary embodiment, the method includes administering to the subject an amount of a composition of any of the invention sufficient to reverse the poor blood flow.

In various embodiments, the invention provides a method of decreasing neurological damage and/or infarcted tissue in tissues suffering from oxygen deficiency. In an exemplary embodiment, the method includes administering to a subject and amount of a composition of the invention sufficient to decrease neurological damage and/or infract in the tissue suffering from oxygen deficiency. In an exemplary embodiment, the method includes administering to the subject an amount of a composition of any of the invention sufficient to reverse the amount of infracted and or neurologically damaged tissue.

Subjects who can receive the oxygen transfer agent, formed by the methods of the invention include mammals, such as a human, non-human primate, a dog, a cat, a rat, a horse or a sheep. Further, subjects, which can receive the oxygen transfer agent includes fetuses (prenatal subject), post-natal subjects, or subjects at time of birth.

A composition of the present invention can be administered into the circulatory system by injecting the composition directly and/or indirectly into the circulatory system of the subject, by one or more injection methods. Examples of direct injection methods include intravascular injections, such as intravenous and intra-arterial injections, and intracardiac injections. Examples of indirect injection methods include intraperitoneal injections, subcutaneous injections, such that the oxygen transfer agent will be transported by the lymph system into the circulatory system or injections into the bone marrow by means of a trocar or catheter. Preferably, the oxygen transfer agent is administered intravenously.

The subject being treated can be normovolemic, hypervolemic or hypovolemic prior to, during, and/or after infusion of the composition of the invention. The composition can be directed into the circulatory system by methods such as top loading and by exchange methods.

A composition of the invention can be administered therapeutically, to treat hypoxic tissue within a subject resulting from many different causes including reduced RBC flow in a portion of, or throughout, the circulatory system, anemia and shock. Further, the oxygen transfer agent can be administered prophylactically to prevent oxygen-depletion of tissue within a subject, which could result from a possible or expected reduction in RBC flow to a tissue or throughout the circulatory system of the subject. The compositions of the invention are of use to therapeutically or prophylactically treat hypoxia.

In an exemplary embodiment, the invention provides for the treatment of illness, injury or insult by administering to a subject an amount of a formulation of the invention sufficient to provide the treatment. The hemoglobin is in the CO form. In an exemplary embodiment, this conjugate is formulated in phosphate buffered saline.

In various embodiments, the PEG-Hb-CO formulation of the invention is used to treat ischemia. An exemplary type of ischemia treatable by this formulation is peripheral ischemia, such as peripheral diabetic ischemia, and the downstream effects of ischemia. As those of skill will appreciate, the compositions of the invention are of use in treating other forms of ischemia as well.

In various embodiments the invention provides for the treatment of illness, injury or insult by administering to a subject an amount of a formulation of the invention sufficient to provide the treatment. The hemoglobin is either deoxygenated or may be in the CO form and is formulated in a hypertonic salt solution. Exemplary salt concentrations of use in these formulations are from about 4% to about 8%, from about 4.5% to about 7.5% or from about 5% to about 7%. Exemplary formulations include about 4%, about 5%, about 6%, about 7% or about 8% salt. In one formulation the salt concentration is 7.5%. In various embodiments, the salt is NaCl. In various embodiments, this formulation is used to treat sickle cell anemia, stroke, myocardial infarct or traumatic brain injury.

In exemplary embodiments, the PEG-Hb-CO of the invention are of use to increase angiogenesis, increase vasodilation, protect heart and kidney from ischemia, activate mitochondrial KATP channels, decrease endothelial leukocyte adhesion and infiltration, decrease activation of macrophages and microglia, and/or protect cerebrovascular vascular reactivity from seizure-induced dysfunction. Accordingly, the invention provides methods of using the compositions of the invention to achieve such results.

Typically, a suitable dose, or combination of doses of oxygen transfer agent of the invention, is an amount which when contained within the blood plasma will result in a total hemoglobin concentration in the subject's blood plasma between about 0.1 to about 10 grams Hb/dl, or from about 1 to about 4 grams Hb/dl or more, if required to make up for large volume blood losses.

The composition of the invention can be administered to a subject in any useful manner. For example, in one embodiment, the composition is administered as a continuous infusion at a predetermined rate for a predetermined time period. In an exemplary embodiment, a loading dose of a composition of the invention is administered over as short of a period as is reasonable. This initial "burst" is followed up by administration of a second amount of the formulation over at least about 6 hours, at least about 12 hours, at least about 18 hours or at least about 24 hours. In various embodiments, the second amount is at least about 60%, at least about 80%, at least about 100% or at least about 120% of the dosage of the initial "burst."

Exemplary compositions of the invention include a PEG-Hb conjugate in an amount of about 3% to about 6%. An exemplary composition includes a PEG-Hb conjugate in an amount of about 4%.

In a broad sense the present invention also provides for the use of a synthetic hemoglobin-water-soluble polymer conjugate-based oxygen transfer agent in the manufacture of a medicament for the reoxygenation of hypoxic tissue. The hypoxia may be due to any insult, injury or disease including, but not limited to surgery, trauma, ischemia, anemia, myocardial infarct, stroke, shock, diabetes, and traumatic brain injury, wherein the oxygen carrying medicament is administered systemically to an individual having or suspected of having one or more tissue with an oxygen deficit.

In each of the methods set forth above, the PEG-Hb can be bound to oxygen, carbon monoxide or to neither. The PEG-Hb itself or the entire formulation can be formulated to be hypotonic, isotonic or hypertonic with respect to the tonicity of the subject's blood.

The following examples are provided to illustrate selected embodiments of the invention and are not to be construed as limiting its scope.

EXAMPLES

Example 1

Purification of Hemoglobin

This first step involves washing the blood cells free of plasma. On the bench scale this was accomplished by repetitive washing, centrifugation and decanting. This process appears more efficient than the vertical continuous flow centrifuge.

The red cells are washed 4x with buffer (1.2% NaCl with 10 mM phosphate, pH 7.8). The red cells are then lysed (the hemoglobin is extracted without true cell lysis) by the slow addition of 1.5 volumes of WFI over a period of 2 hours. The status of lysis (again, hemoglobin extraction) is monitored by sampling conductivity until it is in the range of 5.50-7.00 μS. The % Hb is determined using a Radiometer OSM3 Hemoximeter. The Osmolality is also tested and is in the range of 130-150 mOsmol. Once hemoglobin extraction is complete the content is pressure filtered through a 1 μm cellulose based depth filter, followed by 0.45/0.2 μm sterile polysulfone based filter into a second tank which serves as the reservoir for the next step. The hemoglobin solution is then pumped through a 300 Kd ultrafilter into a jacketed tank at 10° C., which serves as the initial viral removal step and removes high molecular weight proteins.

The hemoglobin is concentrated using a 10 KD MWCO system and then deoxygenated by recirculation through a hollow fiber membrane contactor until the hemoglobin solution has less than 10% $HbO_2$. A stabilizing agent, cysteine, is added near the end of the oxygen removal phase to a final concentration of 5 mM. The stabilizing agent aids in keeping the oxygen level to less than 10% and also acts to protect the hemoglobin during the heat inactivation phase.

Development of a Viral Inactivation/Removal Step During Hemoglobin Production

Before the bovine hemoglobin can be used in a product for humans, procedures are needed to inactivate any potential viral contaminants while maintaining a functionally active protein biologic. The FDA requires viral inactivation of proteins derived from animal products. This is accomplished by exposure to 60° C. until viral inactivation is achieved, in this case for 4 hours. The solution is then cooled and 0.45/0.2μ filtered into a holding tank. This is purified hemoglobin. The product undergoes QC analysis by FPLC (single peak), visible spectral analysis (peaks at 540 nm and 577 nm), SDS gel electrophoresis, % Hb, % $HbO_2$, % MetHb, pH, osmolality, endotoxin, lipids, and free iron.

As described in FIG. 1 mechanically deoxygenated hemoglobin was virally heat inactivated and this heat inactivated bovine hemoglobin was pure. The heat inactivation process of the mechanically deoxygenated hemoglobin with the reducing agent added maintained a low level of MET-Hb (less than 10%), while retaining its integrity, as evidenced by the chart below (Table 1). Exposure to 60° C. for 10 hours had no effect upon the product in the deoxygenated (deoxy) form (with 5 mM cysteine added), in relation to % tHb and % METHb. This was not the case for the bovine hemoglobin in the deoxygenated form without cysteine where approximately 40% of the protein was lost.

TABLE 1

Deoxygenation of hemoglobin stabilizes the product to heat inactivation

| Deoxy Hb + 5 mM Cysteine | | Deoxy Hb without Cysteine[1] | | Hb in CO form + 5 mM Cysteine | | Hb in CO form, without Cysteine | |
| --- | --- | --- | --- | --- | --- | --- | --- |
| Before 60° C. | After 10 hrs at 60° C. | Before 60° C. | After 10 hrs at 60° C. | Before 60° C. | After 10 hrs at 60° C. | Before 60° C. | After 10 hrs at 60° C. |
| tHb = 8.3% | tHb = 8.7% | tHb = 8.8% | tHb = 5.2% | tHb = 9.1% | tHb = 9.1% | tHb = 9.1% | tHb = 8.7% |
| METHb = 0.9% | METHb = 1.6% | METHb = 5.9% | METHb = 2.1% | METHb = 0.8% | METHb = 0.7% | METHb = 6.2% | METHb = 4.2% |
| $HbO_2$ = 5.4% | $HbO_2$ = 4.4% | $HbO_2$ = 6.0% | $HbO_2$ = 6.6% | $HbO_2$ = <0% | $HbO_2$ = <0% | $HbO_2$ = 4.3% | $HbO_2$ = 3.4% |
| HbCO = 3.0% | HbCO = 2.1% | HbCO = 6.0% | HbCO = 6.6% | HbCO = 99.4% | HbCO = 100.8% | HbCO = 89.5% | HbCO = 90.2% |

PEGylation of Hemoglobin

Dilution buffer (25 mM sodium phosphate, 120 mM sodium bicarbonate and 4.5% NaCl, pH 8.0) is added to bring the hemoglobin solution to 4-5% concentration. Hemoglobin is PEGylated using a 17:1 molar ratio of PEG to hemoglobin. The reaction is maintained at pH 7.6-7.8 and the reaction is allowed to proceed for one hour. At this point one of two processes may be used.

Process A 15 mM cysteine is added to stop the reaction. After storing the solution overnight at 4° C., the solution will be dialyzed against 20 volumes of buffer (5.0 mM sodium bicarbonate, 1.0 mM sodium phosphate, 150 mM sodium chloride, 4.7 mM Potassium chloride, 2.5 mM Magnesium sulfate, 0.5 mM Calcium chloride, pH 8.1) using a 50 Kd cutoff membrane. The PEG-Hb is then diluted to 4% Hb, dextrose (5 mg/mL) and cysteine (5 mM) are added, and the solution is circulated through a hollow fiber membrane contactor until the % $HbO_2$ is below 10%. The solution is then aseptically filtered into blood bags. The product will undergo QC analysis by FPLC (single peak), visible spectral analysis (peaks at 540 nm and 577 nm), SDS gel electrophoresis, % Hb, % $HbO_2$, % MetHb, pH, osmolality, endotoxin, lipids, and free iron.

Process B 15 mM cysteine is added to stop the reaction. After storing overnight at 4° C., the solution is dialyzed against 20 volumes of buffer (5.0 mM sodium bicarbonate, 1.0 mM sodium phosphate, 150 mM sodium chloride, 4.7 mM Potassium chloride, 2.5 mM Magnesium sulfate, 0.5 mM calcium chloride, pH 8.1) using a 50 Kd cutoff membrane. The PEG-Hb is then diluted to 4% Hb, dextrose (5 mg/mL) and L-cysteine (5 mM) are added, and the solution is placed into the carbon monoxide form by slowly bubbling carbon monoxide through the solution with constant mixing until the % oxygen is less than '0' and the carbon monoxide (CO) is at 95% or greater. The solution is then aseptically filtered into blood bags. The product undergoes QC analysis by FPLC (single peak), visible spectral analysis (peaks at 540 nm and 577 nm), SDS gel electrophoresis, % Hb, % $HbO_2$, % MetHb, pH, osmolality, endotoxin, lipids, and free iron.

Furthermore, the heat inactivated hemoglobin was PEGylated, and the resulting PEG-Hb was pure and active.

Figure 7:
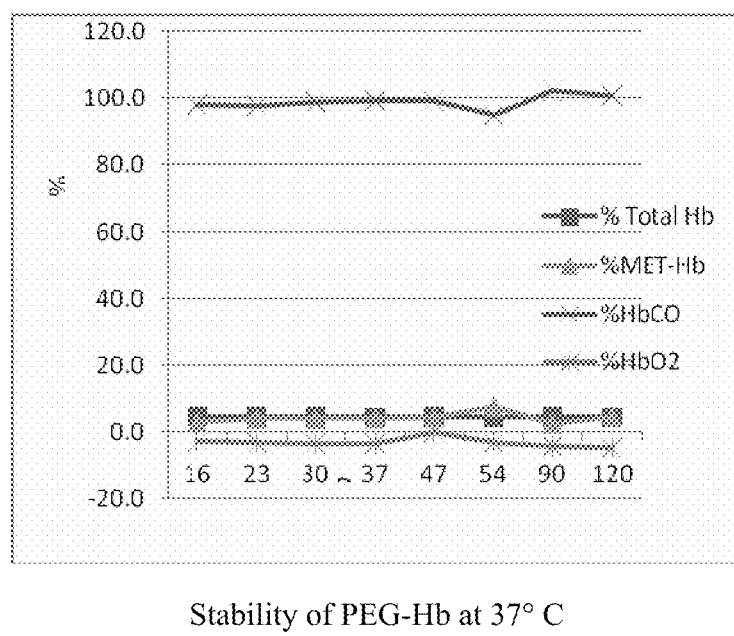
FIG. 7 shows the stability of PEG-Hb at 37° C.

Over a period of 120 days there was no change in the % Total Hb, % MET-Hb, % HbCO, and % HbO2 in the sample stored at 37 C (See FIG. 7).

Development of a Carbon Monoxide Form of PEG-Hb

The goal of these studies was to develop a carbon monoxide (CO) form of the PEG-hemoglobin. This form appears to be particularly stable with regard to keeping % MET-Hb formation low as shown in FIG. 7. This is more stable than the mechanically deoxygenated form.

Furthermore, a CO form of PEG-Hb was stored at 4° C. and only 1.0% was converted to MET-Hb after 8 weeks storage. This same lot of PEG-Hb in the CO form has 1.3% MET-Hb after 12 weeks at 4° C. Furthermore, a CO form of PEG-Hb has been stored at 18° C. for 6 weeks was found to include 7.9% MET-Hb, which rises to 16.7% MET-Hb at the end of 10 weeks at 18° C.

Efficacy of PEG-Hb/HS to Reverse Oxygen Debt

In preliminary studies to test the activity of our PEG-Hb/HS in oxygenating tissues, its ability to increase oxygen delivery to tissues and reverse oxygen debt in a swine model of severe traumatic shock was tested.

Oxygen debt is a measure of the degree of whole body oxygen consumption that is below the level required to maintain aerobic metabolism. It is the one physiologic variable that has been demonstrated to correlate and predict survival, and complications of organ failure after trauma induced hemorrhagic shock. In the model, animals are hemorrhaged to a predetermined oxygen debt to reduce variability between animals, so effects are not dependent on amount of blood loss or endogenous hemoglobin. The model allows for continuous measurement of oxygen consumption ($VO_2$), carbon dioxide production ($VCO_2$), mixed venous hemoglobin oxygen saturation ($SvO_2$), arterial hemoglobin oxygen saturation ($SaO_2$), oxygen extraction ratio (OER), oxygen debt, heart rate, blood pressure, cerebral tissue hemoglobin oxygen saturation ($StO_2$ brain), shoulder skeletal muscle tissue hemoglobin oxygen saturation ($StO_2$ Shoulder), cardiac output (CO) as well as measurement of $PO_2$ in skeletal muscle, liver, intestinal mucosa, oral mucosa, and kidney.

In the model, hemorrhage is accompanied by a bilateral hindlimb skeletal muscle injury and femur fracture to produce combat relevant tissue injury. This type of tissue injury has been demonstrated to independently affect tissue oxygen delivery and result in greater reductions in splanchnic blood flow compared to hemorrhage alone. After skeletal muscle injury and femur injury using a captive bolt, animals are hemorrhaged to a predetermined oxygen debt of 80 mL/kg.

The hemorrhaging to a uniform oxygen debt insures that all animals have limited variability in their final pretreatment injury and greatly reduces the variably in the volume removed as opposed to pressure driven hemorrhages. In these animals, oxygen debt is monitored continuously and cumulatively. Oxygen debt is based on deviations of VO2 below baseline values taken prior to skeletal muscle injury and is measured every 10 seconds.

Following the injury, oxygen debt in the animals climbs during hemorrhage. At a time when 100% of targeted oxygen debt has been reached (80 mL/kg) in the injured animals, the animal received an infusion of 500 cc of PEG-Hb (PEG-Hb concentration of 4% and hypertonic saline solution of 5-7.5%) over a 15 min period of time (resuscitation period). After administration of PEG-Hb, oxygen debt rapidly reverses (averaged results of 4 injured animals). Increases in tissue oxygenation during the resuscitation period paralleled the changes in oxygen debt and then stabilize over a three hour period.

In contrast to PEG-Hb, treatment of 2 animals with 500 mL of hetastarch (Hespan), a standard treatment of trauma patients, produced no reversal of oxygen debt nor did Oxyglobin, an HBOC product being developed by Biopure as a blood substitute. These findings are important because first they show that the treatment currently used for trauma is ineffective in oxygenating tissue and therefore is likely to produce limited effect in patients undergoing hemorrhagic shock. Secondly, they show that one of the products which has been tested extensively in humans and failed in clinical trials, Oxyglobin, failed to oxygenate tissue. The fact that the composition of the invention reversed oxygen debt clearly indicates the composition of the invention and Biopure's are very different and the potential of PEG-Hb/HS in treating trauma should not be judged based on the failure of other HBOC's.

Furthermore, two injured animals treated with 500 cc of packed red blood cells had a reduction in oxygen debt which was expected. However, the magnitude of the reversal did not appear to be as great as that induced by PEG-Hb. Importantly, even if the packed red blood cell treatment produced the same effect as PEG-Hb, these results would support the use of PEG-Hb as a blood substitute since the goal of an HBOC is to be as effective as blood transfusion.

In addition to testing for changes in oxygen debt and oxygen delivery to tissues, we also measured sublingual microcirculation in the hemorrhaged animals as a measure of reperfusion of tissue after hemorrhage. The functional capillary density was also qualitatively measured as the total length of all vessels over the viewed area as a measure of perfusion of the tissues. What is seen is that during hemorrhaging, the capillary density decreases dramatically. In contrast, the PEG-Hb treatment brings the density back near to baseline normal levels near the end of the study. This occurs despite the end hemoglobin level dropping from a baseline of 12.3 g/dl to 7.1 g/dl. As noted, PEG-Hb infusion enhanced functional capillary density to a greater degree than either Hetastarch or packed red cells.

Example 2

Rationale: In the murine model of hind limb ischemia induced by femoral artery ligation, mice with diabetes display significantly impaired restoration of blood flow and angiogenesis responses compared to non-diabetic animals. In this study, we tested the hypothesis that administration of Sanguinate would facilitate restoration of blood flow and angiogenesis.

Method and Results: C57BL/6 mice at age of 6 weeks were rendered diabetic with streptozotocin (stz) and at age of 12 weeks were subjected to FA ligation followed by administration of Sanguinate (20 ml/kg/day) via intraperitoneal (i.p.) injection daily for 4 weeks. Vehicle treated diabetic mice received i.p. injection with equal volumes of 1×PBS daily. Diabetic mice treated with Sanguinate displayed significantly improved blood flow ratios (ischemia/sham) by laser Doppler analysis on day 28 after FA ligation compared to vehicle treated group (63.36±5.83 vs 44.39±4.13 BFR (%), n≥9, p=0.019). Immunohistochemistry staining with CD31 on the muscle tissue demonstrated significantly increased microvessel density in diabetic mice treated with Sanguinate™ on days 28 after FA ligation compared to vehicle treated group (663.86±57.78 vs 461.44±36.19 capillaries/mm$^2$, p<0.0001). Taken together, these data reveal significant therapeutic effects of Sanguinate in diabetic limb ischema in a mouse model and may provide the basis for the use of this agent as complementary vascular-salvaging therapy in long-standing diabetes.

Protocol: C57BL/6 mice were rendered type 1 diabetic with streptozotocin (multiple low-dose injection). One month after induction of diabetes, the mice were subjected to unilateral hind limb ischemia. Blood flow and angiogenesis were monitored in this study.

Procedure: The skin incision was made on the upper thigh of the mouse. The left leg was subjected to the surgical procedure, and the right leg underwent the identical procedure except the femoral artery ligation was not performed. The inguinal ligament and the upper half of the femoral artery were exposed. The vascular bundle was ligated with two sterile 8/0 non-absorbable silk sutures below the inguinal ligament proximally and just above the bifurcation into the superficial and deep femoral arteries distally. All arterial and venous branches connected to the isolated segment of femoral vessels were tied off with 8/0 non absorbable sutures. Finally, the vein and the artery were cut between proximal and distal ligatures. The skin incision was closed with sterile 5/0 nylon suture.

Mouse #s and Groups: Based on our preliminary studies, we began with >15 mice per group to be sure to have sufficient mice at the end of the study and to have sufficient tissue for analysis.

The experiments were staggered in order to perform additional vehicle treated mice.

Group #1—Diabetic WT mice+20 ml/kg/day Sanguinate (IP) beginning immediately after femoral artery ligation Group #2—Diabetic WT mice+PBS (20 ml/kg/day IP)

Endpoints

Laser Doppler Blood Flow Imaging (day 28) Note that blood flow is examined in left (injured) and right leg (sham) and then reported as a ratio left/right. The mean of values of Diabetes/Sanguinate and Diabetes/PBS is reported.

Quantitative assessment of angiogenesis using staining to CD31 and quantitative imaging program (day 28) (left leg)

Data

Endpoint #1: Quantitative Assessment of Angiogenesis

On day 28, mice were sacrificed and hindlimb skeletal muscle in the distribution of the femoral artery ligation retrieved and subjected to immunohistochemistry using anti-cD31 IgG. Serial images were retrieved and image analysis performed to determine the effects of Sanguinate on angiogenesis:

| Group/Treatment | Capillaries/mm$^2$ |
|---|---|
| Sham leg/Vehicle | 805.60 ± 55.60 |
| Sham leg/DRUG | 763.40 ± 9.39 |
| Ischemic Leg/Vehicle | 461.44 ± 36.19* |
| Ischemic Leg/DRUG | 663.86 ± 57.78** |

**indicates p < 0.001 Ischemic Leg/Vehicle
*indicates p < 0.001 vs. Sham Leg/Vehicle Endpoint #2: Blood Flow Recovery % Blood Flow Recovery comparing ligated femoral artery limb/contralateral (Sham) limb was assessed using laser Doppler imaging. In these studies, a ratio is reported between the injured leg and its contralateral sham leg so that the basal vascular dysfunction is taken into account. The data are as follows:

| Group/treatment | % Blood flow recovery |
|---|---|
| Ischemic Leg/Sham VEHICLE | 44.38 ± 12.38 |
| Ischemia Leg/Sham DRUG | 63.36 ± 18.43* |

*indicates p = 0.0187

Conclusion

Administration of Sanguinate to diabetic mice undergoing hind limb ischemia, induced by femoral artery ligation, results in significant improvement in quantification of angiogenesis when compared to findings using vehicle. Administration of Sanguinate to diabetic mice undergoing hind limb ischemia, induced by femoral artery ligation, significantly improves blood flow recovery as measured by Laser Doppler imaging when compared to vehicle (PBS) treatment.

Example 3

The effect of transfusion of PEGylated CO-hemoglobin (PEG-COHb) was evaluated in anesthetized rats subjected to 2 hours of focal cerebral ischemia and 1 day of reperfusion. PEG-Hb was stored in the carboxy state (PEG-COHb) to provide a source of CO and reduce autooxidation and increase the shelf life. Transfusion of 10 ml/kg of PEG-COHb at 20 minutes of ischemia did not alter arterial blood pressure or increase red cell flux in the ischemic core. Plasma hemoglobin increased to only 0.6 g/dL, yet infarct volume was markedly decreased and neurological deficits were improved. Early topload transfusion of PEG-COHb protects the brain from ischemic stroke.

Surgical Preparation

All procedures were approved by the Johns Hopkins University Animal Care and Use Committee. Anesthesia was induced in male Wistar rats (250-350 g) with 5% isoflurane and maintained with approximately 2% isoflurane via nose cone with spontaneous ventilation during surgery. Isoflurane concentration was decreased to approximately 1.5% after surgery. Inspired $O_2$ was approximately 25-30%. Catheters were inserted into a femoral vein for transfusion and into a femoral artery for measuring arterial blood pressure and sampling arterial blood. A heating lamp was used to maintain rectal temperature during ischemia and early reperfusion. A small incision was made in the scalp and a small burr hole was made in lateral parietal bone until only a thin amount of bone remained. A 1-mm diameter fiberoptic probe was secured against the thinned bone. The probe was connected to a laser-Doppler flowmeter which transmits and receives near-infrared light and calculates relative changes in red blood cell flux. The laser-Doppler flux signal was used to assess the adequacy of vascular occlusion during the ischemic period.

Transient focal cerebral ischemia was induced by the intraluminal filament technique to occlude blood flow into the middle cerebral artery. The right common carotid artery was exposed through a lateral incision and occluded. The right external carotid artery was dissected and ligated and the occipital artery branch of the external carotid artery was isolated and coagulated. The proximal pterygopalatine artery branch of the right internal carotid artery was ligated, and a 4-0 monofilament nylon suture (with the tip rounded) was advanced approximately 2 cm into the internal carotid artery. The filament position was adjusted to produce at least a 60% reduction in the laser-Doppler flux signal. After two hours of occlusion, reperfusion was begun by withdrawing the intraluminal suture. After monitoring for the first 30 min of reperfusion, catheters were removed, incisions were closed with suture, and anesthesia was discontinued.

Experimental Design

PEG-albumin and PEG-COHb were synthesized at Prolong Pharmaceuticals (South Plainfield, N.J.). Surface lysine residues on purified bovine Hb were conjugated with 5000 molecular weight PEG. The PEG-Hb solution was bubbled with CO to convert>80% of the PEG-Hb to PEG-COHb before storage. Solutions containing 4-6% protein were stored at 2-10° C. in sterile blood bags. Three groups of 10 rats were studied: 1) no transfusion, 2) bovine PEG-albumin transfusion, and 3) bovine PEG-COHb transfusion. On the day of the experiment, an aliquot of the solution was warmed and transfused as a topload equivalent to 10 ml/kg body weight. The transfusion started at 20 min of MCAO. The rate of intravenous transfusion was 0.5 ml/min and occurred over approximately 5-7 min. Mean arterial pressure and the percent change in laser-Doppler flow was recorded at 15-min intervals during 2 h of MCAO and 30 min of reperfusion. Rectal temperature was monitored through 1 h of reperfusion as the animals recovered from anesthesia in a warm environment. Arterial blood (~0.7 ml) was sampled at baseline, 1 h of MCAO, and 30 min of reperfusion. Arterial blood pH, $PCO_2$, $PO_2$, and electrolytes were measured on a Radiometer blood gas analyzer (ABL80). Arterial Hb concentration, $O_2$ saturation, MetHb, and COHb were measured on a Radiometer Hemoximeter (OSM3). Plasma from the samples was analyzed for Hb concentration. The rats were assessed for neurologic deficits at 1 and 24 h of reperfusion on a 0-4 scale (0=no deficit, 1=failure to extend forelimb during placing, 2=circling, 3=unilateral weakness, and 4=no spontaneous motor activity). At 24 h, the brain was harvested to measure infarct volume. The brain was divided into 7 coronal sections (2 mm thick). The sections were stained with a 1% solution of triphenyltetrazolium chloride, which stains viable regions red. The pale, nonviable areas of cerebral cortex and striatum were measured on the anterior and posterior surfaces of each section. The infarct volume of each section was calculated from the product of the section thickness and the average of the infarct area on the anterior and posterior surfaces. Total infarct volume for cortex and striatum was obtained by summing the volume from each section. Values are expressed as a percent of the entire structure. Measurements were compared among the 3 groups by ANOVA and the Newman-Keuls multiple range test at the 0.05 level of significance. Data are presented as mean±SE.

Results

Arterial pH, $PCO_2$, and $PO_2$ remained stable and in the physiologic range during MCAO and early reperfusion in all groups of rats (Table 1). There were no significant differences among the groups transfused at 20 min of MCAO. Electrolyte concentrations remained similar among the groups after transfusion (Table 2). As expected with a topload protein transfusion, small decreases in hematocrit occurred (Table 3).

TABLE 1

Arterial pH and blood gases during and after 2 h of middle cerebral artery occlusion (MCAO) in groups with no transfusion or transfusion at 20 min of MCAO (mean ± SE; n = 10) Baseline 60 min MCAO 30 min reperfusion

|  | Baseline | 60 min MCAO | 30 min Reperfusion |
| --- | --- | --- | --- |
| pH |  |  |  |
| No transfusion | 7.40 ± 0.01 | 7.41 ± 0.01 | 7.41 ± 0.01 |
| PEG-Abumin | 7.41 ± 0.01 | 7.41 ± 0.01 | 7.39 ± 0.01 |
| PEG-COHb | 7.39 ± 0.01 | 7.40 ± 0.01 | 7.39 ± 0.01 |
| $PCO_2$ (mm Hg) |  |  |  |
| No transfusion | 45.0 ± 0.9 | 43.0 ± 1.0 | 43.6 ± 1.1 |
| PEG-Albumin | 42.0 ± 1.1 | 42.5 ± 0.7 | 45.4 ± 0.5 |
| PEG-COHb | 43.7 ± 0.8 | 44.3 ± 1.4 | 44.3 ± 2.0 |
| $PO_2$ (mm Hg) |  |  |  |
| No transfusion | 120 ± 3 | 123 ± 5 | 124 ± 3 |
| PEG-Albumin | 124 ± 2 | 123 ± 3 | 119 ± 4 |
| PEG-COHb | 128 ± 4 | 122 ± 6 | 125 ± 7 |
| Base Excess |  |  |  |
| No transfusion | 1.6 ± 0.5 | 1.5 ± 0.6 | 1.7 ± 0.4 |
| PEG-Albumin | 1.4 ± 0.3 | 2.1 ± 0.4 | 1.9 ± 0.3 |
| PEG-COHb | 0.3 ± 0.6 | 1.4 ± 0.4 | 1.3 ± 0.3 |

TABLE 2

Arterial blood electrolytes during and after 2 h of MCAO in groups with no transfusion or transfusion at 20 min of MCAO (mean ± SE; n = 10)

|  | Baseline | 60 min MCAO | 30 min reperfusion |
| --- | --- | --- | --- |
| $Na^+$ (mM) |  |  |  |
| No transfusion | 138.4 ± 0.6 | 140.2 ± 1.1 | 141.0 ± 0.8 |
| PEG-Albumin | 140.2 ± 0.5 | 138.2 ± 0.5 | 138.3 ± 0.6 |
| PEG-COHb | 142.0 ± 0.8 | 141.4 ± 0.4 | 142.7 ± 0.7 |
| $K^+$ (mM) |  |  |  |
| No transfusion | 4.1 ± 0.1 | 4.5 ± 0.2 | 4.0 ± 0.1 |
| PEG-Albumin | 4.1 ± 0.1 | 4.1 ± 0.1 | 4.0 ± 0.1 |
| PEG-COHb | 4.0 ± 0.1 | 4.1 ± 0.1 | 4.3 ± 0.1 |
| $Ca^{2+}$ (mM) |  |  |  |
| No transfusion | 1.36 ± 0.04 | 1.23 ± 0.06 | 1.20 ± 0.05 |
| PEG-Albumin | 1.53 ± 0.26 | 1.34 ± 0.02 | 1.30 ± 0.05 |
| PEG-COHb | 1.28 ± 0.04 | 1.24 ± 0.02 | 1.21 ± 0.03 |
| $Cl^-$ (mM) |  |  |  |
| No transfusion | 100.2 ± 0.7 | 100.7 ± 1.5 | 101.6 ± 0.7 |
| PEG-Albumin | 102.8 ± 1.0 | 101.7 ± 0.5 | 101.1 ± 0.5 |
| PEG-COHb | 104.0 ± 1.0 | 102.0 ± 0.6 | 102.5 ± 0.7 |

TABLE 3

Whole blood hemoglobin analysis during and after 2 h of MCAO in groups with no transfusion or transfusion at 20 min of MCAO (mean ± SE; n = 10)

|  | Baseline | 60 min MCAO | 30 min reperfusion |
|---|---|---|---|
| Hematocrit (%) | | | |
| No transfusion | 37 ± 1 | 37 ± 1 | |
| PEG-Albumin | 38 ± 1 | 34 ± 1 | |
| PEG-COHb | 36 ± 1 | 33 ± 1 | |
| Hemoglobin (g/dL) | | | |
| No transfusion | 12.5 ± 0.3 | 11.7 ± 0.3 | 12.1 ± 0.3 |
| PEG-Albumin | 12.5 ± 0.2 | 11.2 ± 0.4 | 11.2 ± 0.3 |
| PEG-COHb | 11.7 ± 0.3 | 11.1 ± 0.3 | 11.1 ± 0.6 |
| Arterial $O_2$ content (ml $O_2$/dL) | | | |
| No transfusion | 16.0 ± 0.3 | 15.3 ± 0.3 | 16.3 ± 0.4 |
| PEG-Albumin | 16.3 ± 0.2 | 14.4 ± 0.4 | 14.1 ± 0.7 |
| PEG-COHb | 14.9 ± 0.7 | 14.8 ± 0.6 | 14.4 ± 0.7 |
| MetHb (%) | | | |
| No transfusion | 1.0 ± 0.1 | 0.9 ± 0.1 | 0.7 ± 0.1 |
| PEG-Albumin | 0.9 ± 0.1 | 0.9 ± 0.1 | 0.9 ± 0.1 |
| PEG-COHb | 0.7 ± 0.1 | 1.6 ± 0.2* | 1.5 ± 0.1* |
| COHb (%) | | | |
| No transfusion | 0.6 ± 0.1 | 0.5 ± 0.1 | 0.3 ± 0.3 |
| PEG-Albumin | 0.5 ± 0.1 | 0.4 ± 0.1 | 0.2 ± 0.1 |
| PEG-COHb | 0.6 ± 0.1 | 2.3 ± 0.2* | 2.3 ± 0.1* |

*$P < 0.05$ from PEG-Albumin

Figure 3:
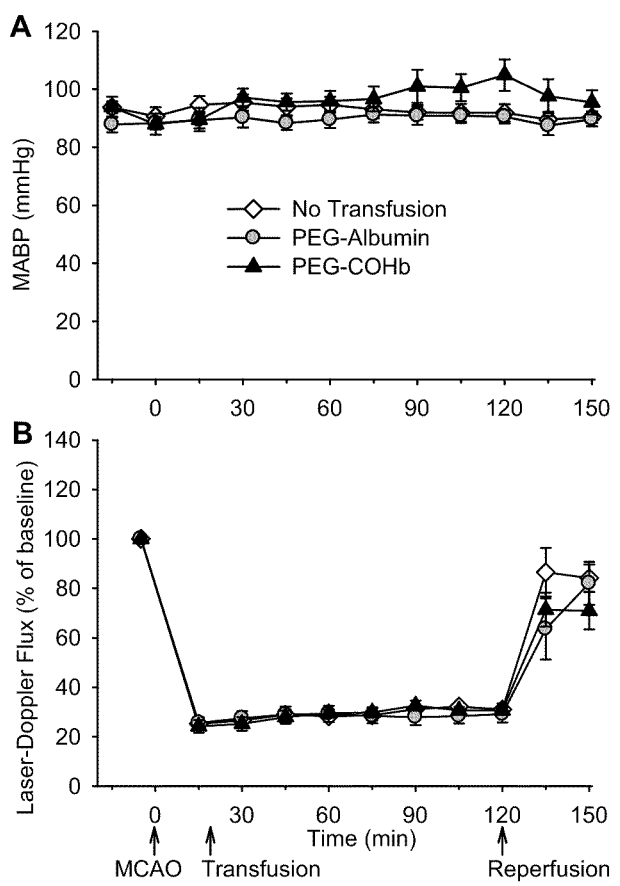
FIG. 3 shows arterial blood pressure (A) and laser-Doppler flux, measured over lateral parietal cortex and expressed as a percent of baseline (B), during 2 h of middle cerebral artery occlusion (MCAO) and the first 30 min of reperfusion in groups of rats undergoing either no transfusion or transfusion with 10 ml/kg of PEG-albumin or PEG-COHb at 20 min of MCAO (mean±SE; n=10 per group).
Figure 4:
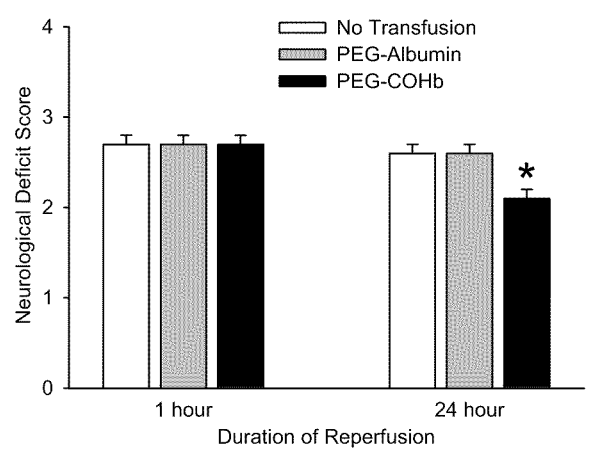
FIG. 4 shows neurologic deficit score on a 0-4 scale (0=no deficit) at 1 or 24 h of reperfusion after 2 h of MCAO in groups with no transfusion or transfusion of PEG-albumin or PEG-COHb at 20 min of MCAO (mean±SE; n=10). * $P<0.05$ between PEG-COHb groups versus no transfusion and PEG-albumin groups.
Figure 5:
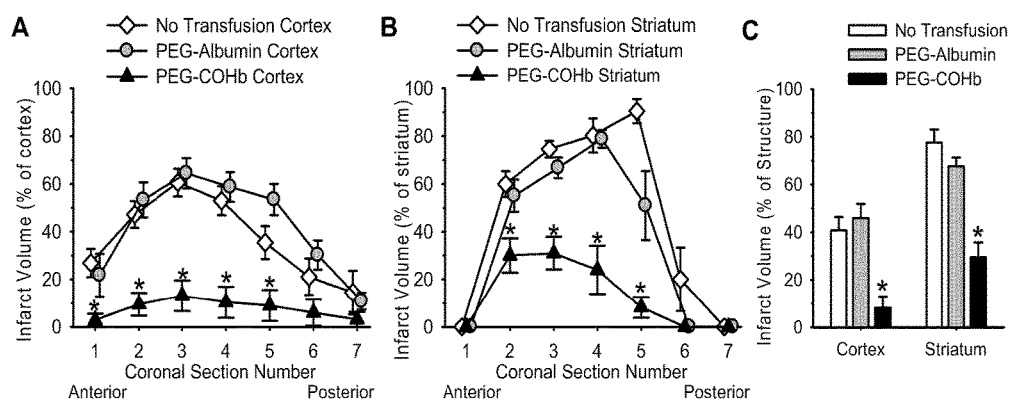
FIG. 5 is a graphic display of infarct volume in each of the 7 coronal sections for cerebral cortex (A) and striatum (B), and total infarct volume summed over the 7 sections for cerebral cortex and striatum (C). Values are expressed as a percent of the contralateral total structure (means±SE; n=10). * $P<0.05$ between PEG-COHb group versus no transfusion and PEG-albumin groups.
Figure 6:
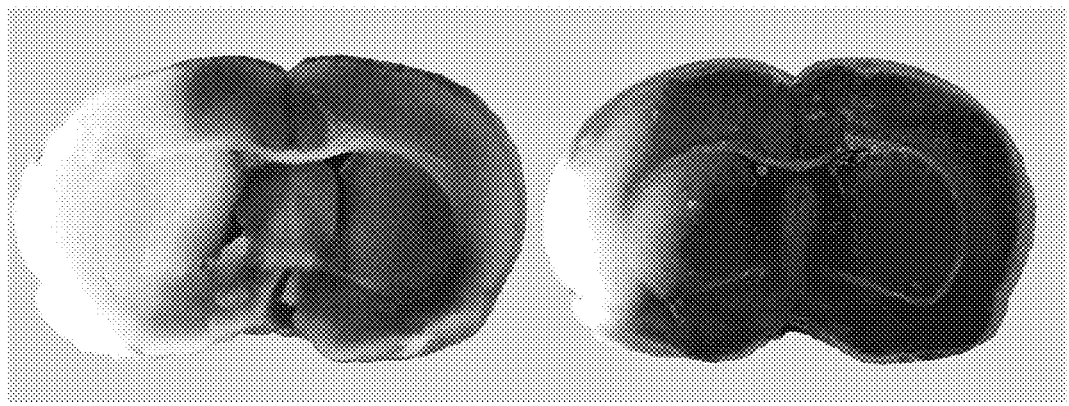
FIG. 6 shows that the amount of viable brain tissue (stained dark) is greater in rats transfused with PEG-COHb (right image) of the invention, than in a control rat not infused with PEG-COHb of the invention (left image).

However, there were no significant differences in hematocrit or whole blood Hb concentration in the PEG-COHb-transfused group compared to the PEG-albumin-transfused group. The percents of MetHb and COHb in whole blood were slightly elevated after transfusion of PEG-COHb (Table 3). Analysis of plasma Hb at 60 min of MCAO (about 35 min after completing the PEG-COHb transfusion) indicated concentrations of 0.6±0.1 g/dL (±SE), and the level remained relatively unchanged at 30 min of reperfusion. The percent of COHb in the plasma Hb was in the 11±4% at 60 min of MCAO and 6±1% at 30 min of reperfusion. Values for mean arterial blood pressure are shown in FIG. 3A. Although there was tendency for pressure to increase slightly during prolonged MCAO in the PEG-COHb group, the values were not significantly different among groups at any time point. Laser-Doppler flow was monitored over the lateral cortex where ischemia is most dense. Values are displayed in FIG. 3B. In all groups, flow decreased to approximately 25% of baseline initially and increased slightly over time to approximately 30% of baseline. With reperfusion, flow was restored to approximately 80% of baseline in all groups. There were no significant differences among groups at any time point. Rectal temperature was maintained in the range of 36.5-37.0° C. during ischemia and at 1 h of reperfusion after the rats awoke from anesthesia. Moreover, the rats did not display fever at 24 h. After awakening from anesthesia, neurologic deficit scores were similar among groups (FIG. 4). However, upon retesting at 24 h, neurologic deficit scores improved selectively in the PEG-COHb group. Values for infarct volume at each coronal level and total infarct volumes are shown in FIG. 5. Infarct volume was similar in the group without transfusion and the group transfused with PEG-albumin. Infarct volume was significantly reduced in the group transfused with PEG-COHb compared to either the non-transfused or PEG-albumin group. In the PEG-COHb group, infarct volume was reduced by 82% in cortex and 56% in striatum relative to the PEG-albumin group (FIG. 6). The reduction in infarct volume was present in each of the 5 most anterior slices, thereby indicating that tissue rescue was widespread over the entire middle cerebral artery distribution area.

Discussion

The degree of tissue rescue by PEG-COHb topload transfusion during transient focal cerebral ischemia is substantially greater than that reported with hypervolemic exchange transfusion with αα-crosslinked Hb in rats or polymeric Hb in mice. This finding is remarkable because the plasma Hb concentration attained with the 10 ml/kg topload was 0.6 g/dL, which is considerably less than the 2-2.5 g/dL typically attained with 30-40% exchange transfusion of fluids containing 6 g/dL of Hb. Moreover, increasing the plasma concentration of αα-crosslinked Hb further by increasing the concentration of Hb in the transfusion fluid from 10 g/dL to 20 g/dL produces additional reductions in infarct volume. These comparisons suggest that PEG-COHb may be superior per mole of heme compared to αα-crosslinked Hb and polymeric Hb in rescuing the brain from stroke. The results indicate that large plasma concentrations of PEGylated COHb are not required to rescue the brain. The theoretical advantage of exchange transfusion is that whole blood viscosity can be reduced by decreasing hematocrit and thereby promote collateral blood flow. The advantage of the topload over the exchange transfusion is that this protocol would be easier to implement in clinical stroke and the 10 ml/kg volume is readily tolerated without producing marked hypervolemic-induced hypertension. Significant hypertension was not observed in the present study. Rescue by the PEG-COHb did not appear to be related to an increase in blood flow in the ischemic core of cortex as assessed by laser-Doppler flowmetry at a single site. However, it is possible that collateral blood flow was improved in the ischemic border region sufficient to salvage tissue. The viscosity of the PEGylated Hb solution is closer to that of whole blood compared to solutions of crosslinked and polymeric Hb and thus may better maintain endothelial shear stress and associated NO production, which could help maintain dilation of collateral arteries.

The 10-ml/kg topload transfusion of PEG-albumin and PEG-COHb produced approximately 8-10% decreases in hematocrit. This relatively small decrease in hematocrit will have only a small effect on blood viscosity and is unlikely to improve perfusion sufficiently to reduce brain injury by reducing blood viscosity. The lack of a difference in infarct volume between the group transfused with PEG-albumin and the group with no transfusion in this study and in a previous study with greater hemodilution support this premise. Moreover, the increase in plasma [Hb] to 0.6 g/dL after PEG-COHb topload was inadequate to offset the decrease in hematocrit. Thus, whole blood [Hb] and arterial $O_2$ content were not increased by PEG-COHb transfusion. However, even in the absence of an increase in arterial $O_2$ content or blood flow, an $O_2$ carrier in the plasma may be capable of enhancing $O_2$ delivery to ischemic tissue for several reasons. First, oxygen solubility in plasma is low and represents a major site of resistance of $O_2$ diffusion between the red cell and mitochondria in the tissue. By carrying a large amount of $O_2$ in the plasma, $O_2$ transport from the red cell membrane to the endothelium is facilitated. In this regard, efficacy of transfusion of Hb polymers during MCAO is lost when the solution primarily contains polymers of molecular weight greater than 14 MDa. The current bovine PEG-Hb with approximately 8-10 side chains of 5000 molecular weight PEG appears to represent a good balance of being small enough to have high mobility for facilitating $O_2$ transport in the plasma but large enough to limit extravasation. Second, red cell flux through individual microvessels is heterogeneous and this heterogeneity is amplified under conditions of low perfusion pressure during incomplete ischemia. By delivering $O_2$ through the flow of plasma in capillaries that are red cell deprived, $O_2$ delivery may become more homogenous among capillaries. Third, red cells are particulate and their surface area does not cover the entire surface area of capillary endothelium at any one instant. An $O_2$ carrier in the plasma increases the effective surface area for $O_2$ diffusion. Therefore, a topload infusion of cell-free Hb could invoke several mechanisms of $O_2$ delivery independent of bulk arterial $O_2$ content and macroscopic blood flow.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. An aqueous pharmaceutical formulation capable of delivering oxygen or carbon monoxide (CO) to tissue of a subject to whom said formulation is administered, said formulation comprising a covalent conjugate between a functional, native hemoglobin molecule and at least one molecule of poly(ethylene glycol), said formulation comprising:
   a. a water-soluble hemoglobin fraction comprising a group of bovine hemoglobin molecules wherein each member of said group of bovine hemoglobin molecules
      i. is bound to CO;
      ii. is covalently conjugated to at least one molecule of said poly(ethylene glycol) through an amine moiety of an amino acid residue;
      iii. is substantially free of chemical cross-linking agents;
      iv. includes less than 5% cross-linked hemoglobin; and
      iv. has a $P_{50}$ of from about 9 mm Hg to about 14 mm Hg; and
   b. a water-soluble stabilizer fraction rendering said group of bovine hemoglobin molecules oxidation resistant, said water-soluble stabilizer fraction comprising, a stabilizing agent comprising a structural element more reactive with oxygen than said group of bovine hemoglobin molecules; and
   c. an aqueous diluent fraction comprising, a pharmaceutically acceptable aqueous diluent in which said hemoglobin fraction is soluble, said formulation being essentially free of viral activity, and stably comprising less than about 10% methemoglobin after storage at 45° C. for at least about 4 days.

2. The formulation according to claim 1 wherein each member of said group of bovine hemoglobin molecules is covalently conjugated to five or more molecules of said poly(ethylene glycol) through said amine moiety of five or more of said amino acid residues.

3. The formulation according to claim 1 wherein said amine moiety of said amino acid residue is an ε-amine moiety of a lysine residue.

4. The formulation according to claim 1 wherein said stabilizing agent is an amino acid.

5. The formulation according to claim 4 wherein said stabilizing agent is cysteine.

6. The formulation of claim 1, wherein said aqueous diluent fraction comprises a phosphate buffered saline diluent.

7. The formulation of claim 1, wherein said aqueous diluent fraction comprises a hypertonic saline diluent.

8. The pharmaceutical formulation according to claim 7 wherein said hypertonic saline diluent includes NaCl at a concentration of from about 2.5% to about 7.5%.

9. The formulation according to claim 1, said formulation stably comprising less than about 10% methemoglobin after storage at 45° C. for at least about 15 days.

* * * * *